(12) United States Patent
Medina Padilla et al.

(10) Patent No.: US 8,158,661 B2
(45) Date of Patent: Apr. 17, 2012

(54) GSK-3 INHIBITORS

(75) Inventors: Miguel Medina Padilla, Madrid (ES); Mercedes Alonso Cascon, Madrid (ES); Isabel Dorronsoro Diaz, Madrid (ES); Ana Martinez Gil, Madrid (ES); Gema Panizo Del Pliego, Madrid (ES); Ana Fuertes Huerta, Madrid (ES); Maria Jose Perez Puerto, Madrid (ES)

(73) Assignee: Noscira, S.A. (ES)

( * ) Notice: Subject to any disclaimer, the term of this patent is extended or adjusted under 35 U.S.C. 154(b) by 5 days.

(21) Appl. No.: 12/428,442

(22) Filed: Apr. 22, 2009

(65) Prior Publication Data

US 2009/0233971 A1    Sep. 17, 2009

Related U.S. Application Data

(63) Continuation of application No. 11/098,610, filed on Apr. 5, 2005, now Pat. No. 7,531,561.

(30) Foreign Application Priority Data

Apr. 5, 2004   (EP) .................................... 04075997

(51) Int. Cl.
   *A61K 31/41*    (2006.01)
   *C07D 285/08*   (2006.01)
(52) U.S. Cl. ...................................... 514/361; 548/130
(58) Field of Classification Search .................. 514/361; 548/130
   See application file for complete search history.

(56) References Cited

U.S. PATENT DOCUMENTS

| | | | |
|---|---|---|---|
| 6,872,737 B2 | 3/2005 | Gil et al. | |
| 7,531,561 B2 * | 5/2009 | Padilla et al. | 514/361 |
| 7,666,885 B2 * | 2/2010 | Martinez et al. | 514/362 |

FOREIGN PATENT DOCUMENTS

WO    WO 01/85685    * 11/2001

OTHER PUBLICATIONS

Alonzo, M. et al., "GSK-3 Inhibitors: Discoveries and Developments," Current Medical Chemistry, 11:753-761, 2004.
M$^a$ Mercedes Alonso Cascón, "Tesis Doctoral: Farmacos Modificadores De La Enfermedad De Alzheimer: 1,2,4-Tiadiazolidin-3,5-Dionas (TDZDs) Primeros Inhibidores ATP-NO Competitivos De GSK-3" Universidad Autónoma De Madrid, 2003, chapters 1 and 5.
Martinez, A, et al., "Glycogen Synthase Kinase 3 (GSK-3) Inhibitors as New Promising Drugs for Diabetes, Neurodegeneration, Cancer and Inflammation," Medicinal Research Reviews, 22(4):1-12, 2002.
Martinez, A., et al., "First Non-ATP Competitive Glycogen Synthase Kinase 3β (GSK-3β) Inhibitors: Thiadiazolidinones (TDZD) as Potential Drugs for the Treatment of Alzheimer's Disease," J. Med. Chem., 45:1292-1299, 2002.
Andrew et al., "The Determination of Hydroxydopamines and Other Trace Amines in the Urine of Parkinsonian Patients and Normal Controls," Neurochem. Res. 18(11), pp. 1175-1177, 1993, Abstract only.
Ashcroft et al., "The Selective and Inducible Activation of Endogenous PI 3-Kinase in PC12 Cells Results in Efficient NGF-Mediated Survival but Defective Neurite Outgrowth," Oncogene, 18, pp. 4586-4597, 1999.
Avila, "Tau Aggregation into Fibrillar Polymers: Taupathies," FEBS Lett., 476, pp. 89-92, 2000.
Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," J. Pharmacol. Exp. Ther. 279, 1453-1461, 1996, Abstract only.
Badorff et al., "Fas Receptor Signaling Inhibits Glycogen Synthase Kinase 3β and Induces Cardiac Hypertrophy Following Pressure Overload," J. Clin. Invest., 109(3), pp. 373-381, 2002.
Ballin et al., "The Effect of Lithium Chloride on Tumour Appearance and Survival of Melanoma-Bearing Mice," Br. J. Cancer., 48(1), pp. 83-87, 1983.
Bancher et al., "On the Relationship Between Measles Virus and Alzheimer Neurofibrillary Tangles in Subacute Sclerosing Panencephalitis," Neurobiol. Of Aging 17(4), pp. 527-533, Jul. 1996, Abstract only.
Behrens et al., "Amino-Terminal Phosphorylation of c-Jun Regulates Stress-Induced Apoptosis and Cellular Proliferation," Nat. Genet. 21:326-329, 1999, Abstract only.

(Continued)

*Primary Examiner* — Rei-tsang Shiao
(74) *Attorney, Agent, or Firm* — Kenneth H. Sonnenfeld; King & Spalding

(57) ABSTRACT

Provided are thiadiazolidine compounds of formula I

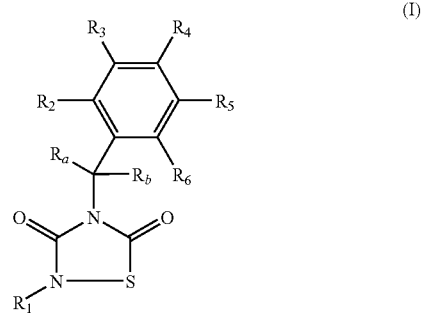

(I)

wherein $R_1$ is an organic group having at least 8 atoms selected from C or O, which is not linked directly to the N through a —C(O)— and comprising at least an aromatic ring, and their pharmaceutical compositions. These compounds are selective GSK-3 inhibitors and have improved bioavailability. They are useful for the treatment of GSK-3 mediated diseases, among others Alzheimer's disease, type II diabetes, depression and brain injury.

52 Claims, No Drawings

OTHER PUBLICATIONS

Bienz et al., "Linking Colorectal Cancer to Wnt Signaling Review," Cell, 103, pp. 311-320, Oct. 13, 2000. Bijur et al., "Glycogen Synthase Kinase-3β Facilitates Staurosporine-and Heat Shock-induced Apoptosis," J. Biol. Chem., 275, pp. 7583-7590, 2000.

Breton et al., "The Natural Product Hymenialdisine Inhibits Interleukin-8 Production in U937 Cells by Inhibition of Nuclear Factor-$_K$B," J Pharmacol Exp Ther., 282(1), pp. 459-466, 1997.

Buée et al., "Tau Protein Isoforms, Phosphorylation and Role in Neurodegenerative Disorders," Brain Research Reviews, 33, pp. 95-130, 2000.

Carmichael et al., "Glycogen Synthase Kinase-3β Inhibitors Prevent Cellular Polyglutamine Toxicity Caused by the Huntington's Disease Mutation," The Journal Of Biological Chemistry, 277(37), pp. 33791-33798, Sep. 13, 2002.

Chalecka-Franaszek et al., "Lithium Activates the Serine/Threonine Kinase Akt-1 and Suppresses Glutamate-Induced Inhibition of Akt-1 Activity in Neurons," Proc. Natl. Acad. Sci., 96, pp. 8745-8750, 1999.

Chen et al., "The Mood-Stabilizing Agent Valproate Inhibits the Activity of Glycogen Synthase Kinase-3," J. Neurochem., 72, pp. 1327-1330, 1999.

Cohen, "The Role of Protein Phosphorylation in Human Health and Disease," Eur. J. Biochem., 268, pp. 5001-5010, 2001.

Crocker et al., "C-Jun Mediates Axotomy-Induced Dopamine Neuron Death in vivo," Proc. Natl. Acad. Sci. USA, 98, pp. 13385-13390, Nov. 6, 2001.

Cross et al., "Selective Small-Molecule Inhibitors of Glycogen Synthase Kinase-3 Activity Protect Primary Neurones From Death," J.Neurochem. 77, pp. 94-102, 2001.

Curtius et al., "Mass Fragmentography of Dopamine and 6-Hydroxydopamine: Application to the Determination of Dopamine in Human Brain Biopsies from the Caudate Nucleus," J. Chromatogr. 99, 529-540, 1974, Abstract only.

De Sarno et al., "Lithium Prevents and Ameliorates Experimental Autoimmune Encephalomyelitis," J. Immunol., 181(1), pp. 338-345, Jul. 1, 2008.

Dou et al., "Neuroprotective Activities of Sodium Valproate in a Murine Model of Human Immunodeficiency Virus-1 Encephalities," J. Neurosci., 23(27), pp. 9162-9170, 2003.

Dou et al., "Neuroprotective Strategies for HIV-1 Associated Dementia," Neurotox Res., 6 (7-8), pp. 503-521, 2004.

Eldar-Finkelman et al., "Increased Glycogen Synthase Kinase-3 Activity in Diabetes and Obesity-Prone C57BL/6J Mice," Diabetes, 48, pp. 1-5, Aug. 1999.

Engelender et al., "Synphilin-1 Associates with α-Synuclein and Promotes the Formation of Cytosolic Inclusions," Nat Genet., 22: 110-114, 1999, Abstract only.

Everall et al., "Lithium Ameliorates HIV-gp120-Mediated Neurotoxicity," Mol. Cell. Neurosci., 21, pp. 493-501, 2002.

Ferrer et al., "Active, Phosphorylation-Dependent Mitogen-Activated Protein Kinase (MARK/ERK), Stress-Activated Protein Kinase/c-Jun N-Terminal Kinase (SAPK/JNK), and p38 Kinase Expression in Parkinson's Disease and Dementia with Lewy Bodies," J Neural Transm., 108, pp. 1383-1396, 2001.

Fishman et al., "Evidence for Involvement of Wnt Signaling Pathway in IB-MECA Mediated Suppression of Melanoma Cells," Oncogene, 21, pp. 4060-4064, 2002.

Frame et al., "GSK3 Takes Centre Stage More than 20 Years After Its Discovery," Biochem. J., 359, pp. 1-16, 2001.

Fujiwara et al., α-Synuclein is Phosphorylated in Synucleinopathy Lesions, Nature Cell Biology 4, 160-164, 2002, Abstract only.

Gallicchio, "Effect of Lithium on Blood Cells and the Function of Granulocytes," in "Lithium and the Cell", ed. Birch, N. J. (Academic, San Diego), pp. 185-198, 1991.

Geddes et al., "Pathological Overlap in Cases of Parkinsonism Associates with Neurofibrillary Tangles," Brain, 116, pp. 281-302, 1993.

Gotoh et al., "Cyclin D1 Over-Expression Correlates with β-catenin Activation, But Not With H-ras Mutations, and Phosphorylation of Akt, GSKβ and ERK1/2 in Mouse Hepatic Carcinogenesis," Carcinogenesis, 24(3), pp. 435-442, 2003.

Grimes et al., "The Multifaceted Roles of Glycogen Synthase Kinase 3β in Cellular Signaling," Prog. Neurobiol. 65, 391-426, 2001, Abstract only.

Gross et al., "Opioid-Induced Cardioprotection Occurs via Glycogen Synthase Kinase β Inhibition During Reperfusion in Intact Rat Hearts," Circ. Res., 94, pp. 960-966, 2004.

Hall et al., "Valproate Regulates GSK-3-Mediated Axonal Remodeling and Synapsin I Clustering in Developing Neurons," Mol. Cell. Neurosci., 20, 257-270, Jun. 2002, Abstract only.

Haefner, "NF-kB Arresting a Major Culprit in Cancer," Drug Discov Today 7:653-663, Jun. 2002, Abstract only.

Hasegawa et al., "Phosphorylated α-Synuclein Is Ubiquitinated in α-Synucleinopathy Lesions," The Journal Of Biological Chemistry, 277(50),pp. 49071-49076, Dec. 13, 2002.

Hauw et al., "Constant Neurofibrillary Changes in the Neocortex in Progressive Supranuclear Palsy. Basic Differences with Alzheimer's Disease and Aging," Neurosci. Lett. 119(2), pp. 182-186, Nov. 13, 1990, Abstract only.

Hirano et al., "Amyotrophic Lateral Sclerosis and Parkinsonism-Dementia Complex on Guam," Arch. Neurol. 15(1), pp. 35-51, Jul. 1966, Abstract only.

Ho et al., "The Molecular Biology of Huntington's Disease," Psychol. Med., 31(3), pp. 3-14, 2001, Abstract only.

Hoeflich et al., "Requirement for Glycogen Synthase Kinase-3β in Cell Survival and NF-$_K$B Activation,"Nature, 406:86-90, 2000, Abstract only.

Hof, et al., "Differential Distribution of Neurofibrillary Tangles in the Cerebral Cortex of Dementia Pugilistica and Alzheimer's Disease Cases, " Acta Neuropathol. 85:23-30, 1992, Abstract only.

Hof et al., "Quantitative Neuropathologic Analysis of Pick's Disease cases: Cortical Distribution of Pick Bodies and Coexistence with Alzheimer's Disease," Acta Neuropathol. 87:115-124, 1994.

Holtz et al., "Parkinsonian Mimetics Induce Aspects of Unfolded Protein Response in Death of Dopaminergic Neurons," J. Biol. Chem., 278(21), pp. 19367-19377, May 23, 2003.

Hongisto et al., "Lithium Blocks the c-Jun Stress Response and Protects Neurons via Its Action on Glycogen Synthase Kinase 3," Molecular and Cellular Biology, 23(17), pp. 6027-6036, Sep. 2003.

Hu et al., "Keratinocyte Adherens Junctions Initiate Nuclear Signaling by Translocation of Plakoglobin from the Membrane to the Nucleus," The Journal Of Investigative Dermatology, 121(2), pp. 242-251, 2003.

Hu et al., "Protein Kinase and Protein Phosphatase Expression in Amyotrophic Lateral Sclerosis Spinal Cord," Journal of Neurochemistry, 85, pp. 432-442, 2003.

Imai et al., "An Unfolded Putative Transmembrane Polypeptide, which Can Lead to Endoplasmic Reticulum Stress, Is a Substrate of Parkin," Cell, 105, pp. 891-902, Jun. 29, 2001.

Jope RS et al., "Lithium and Brain Signal Transduction Systems," Biochem Pharmacol. 47(3), pp. 429-441, 1994.

Jope et al., "Mood Stabilizers, Glycogen Synthase Kinase-3β and Cell Survival," Molecular Psychiatry, 7, pp. S35-S45, 2002.

Kaytor et al., "The GSK3β Signaling Cascade and Neurodegenerative Disease," Curr. Opin. Neurobiol. 12(3), pp. 275-278, Jun. 1, 2002, Abstract only.

Klein et al., "A Molecular Mechanism for the Effect of Lithium on Development," Proc. Natl. Acad. Sci. USA, 93, pp. 8455-8459, Aug. 1996.

Kramlinger, et al., "Addition of Lithium Carbonate to Carbamazepine: Hemoatological and Thryroid Effects," Am. J. Psychiatry 147, 615-620, 1990, Abstract only.

Lee et al., "Neurodegenerative Tauopathies," Annu Rev Neurosci, 24, pp. 1121-1159, Mar. 2001, Abstract only.

Lee et al., "Overexpression of Cellular Activity and Protein Level of Protein Kinase F$_A$/GSK-3α Correlates With Human Thyroid Tumor Cell Dedifferentiation," J Cell Biochem., 58(4), pp. 474-480, 1995.

Levine et al., "Inhibition of Experimental Allergic Encephalomyelitis by Lithium Chloride: Specific Effect or Nonspecific Stress?" Immunopharmacology, 22, pp. 207-213, 1991.

Li et al., "Glucose Enhances Human Macrophage LOX-1 Expression: Role for LOX-1 in Glucose-Induced Macrophage Foam Cell Formation," Circ. Res., 94, pp. 892-901, 2004.

Linseman et al., "A Myocyte Enhancer Factor 2D (MEF2D) Kinase Activated During Neuronal Apoptosis is a Novel Target Inhibited by Lithium," J. Neurochem., 85, pp. 1488-1499, 2003.

Maggirwar et al., "HIV-1 Tat-Mediated Activation of Glycogen Synthase Kinase-3β Contributes to Tat-Mediated Neurotoxicity," J. Neurochem., 73, pp. 578-586, 1999.

Manoukian et al., "Role of Glycogen Synthase Kinase-3 in Cancer: Regulation by Wnts and Other Signaling Pathways," Adv. Cancer Res., 84, 203-29, 2002, Abstract only.

Mann et al., "Alzheimer's Presenile Dementia, Senile Dementia of Alzheimer Type and Down's Syndrome in Middle Age Form an Age Related Continuum of Pathological Changes," Neuropathology and Appl. Neurobiol. 10(3), 185-207, May 1984, Abstract only.

Martin et al., "Toll-Like Receptor-Mediated Cytokine Production is Differentially Regulated by Glycogen Synthase Kinase 3," Nat Immunol., 6(8), pp. 777-784, Aug. 2005.

Martinez et al., "Gylcogen Synthase Kinase 3 (GSK-3) Inhibitors as New Promising Drugs for Diabetes, Neurodegeneration, Cancer, and Inflammation," Med. Res. Rev., 22(4), pp. 373-384, 2002.

Mattson, "Apoptosis in Neurodegenerative Disorders," Nat. Rev. Mol. Cell Biol., 1, pp. 120-129, Oct. 2000.

Mazor et al., "Inhibition of Glycogen Synthase Kinase-3 Represses Androgen Receptor Activity and Prostate Cancer Cell Growth," Oncogene, 23, pp. 7882-7892, 2004.

Meier et al., "Inactivation and Dephosphorylation of Protein Kinase Bα (PKBα) Promoted by Hyperosmotic Stress," EMBO J. 17(24), pp. 7294-7303, 1998.

Noshita et al., "Akt Phosphorylation and Neuronal Survival after Traumatic Brain Injury in Mice," Neurobiology of Disease 9(3), pp. 294-304, Apr. 2002, Abstract only.

Noshita et al., "Evidence of Phosphorylation of Akt and Neuronal Survival After Transient Focal Cerebral Ischemia in Mice," J. Cereb. Blood Flow Metab., 21, pp. 1442-1450, 2001.

Pap et al., "Role of Glycogen Synthase Kinase-3 in the Phosphatidylinositol 3-Kinase/Akt Cell Survival Pathway," J. Biol. Chem., 273, pp. 19929-19932, 1998.

Park et al., "Constitutively Active Glycogen Synthase Kinase-3β Gene Transfer Sustains Apoptosis, Inhibits Proliferation of Vascular Smooth Muscle Cells, and Reduces Neointima Formation After Balloon Injury in Rats," Arteriosclerosis, Thrombosis, and Vascular Biology, 23, pp. 1364-1369, 2003.

Parker et al., "Glycogen Synthase from Rabbit Skeletal Muscle; Effect of Insulin on the State of Phosphorylation of the Seven Phosphoserine Residues in vivo," Eur. J. Biochem., 130, pp. 227-234, 1983.

Paschen et al., "Endoplasmic Reticulum Dysfunction—a Common Denominator for Cell Injury in Acute and Degenerative Diseases of the Brain?" J. Neurochem., 79, 719-725, 2001.

Paulson, "Human Genetics '99: Trinucleotide Repeats, Protein Fate in Neurodegenerative Proteinopathies: Polyglutamine Diseases Join the (Mis)Fold," Am. J. Hum. Genet., 64, pp. 339-345, 1999, Abstract only.

Paulus et al., "Corticonigral Degeneration with Neuronal Achromasia and Basal Neurofibrillary Tangles, " Acta Neuropathol. 81:89-94, 1990, Abstract only.

Peifer et al., "Wnt Signaling in Oncogenesis and Embryogenesis—a Look Outside the Nucleus," Science 287(5458), pp. 1606-1609, Mar. 3, 2000, Abstract only.

Pérez et al., "Chronic Lithium Treatment Decreases Mutant Tau Protein Aggregation in a Transgenic Mouse Model," Journal of Alzheimer's Disease, 5, pp. 301-308, 2003.

Phiel et al., "GSK-3α Regulates Production of Alzheimer's Disease Amyloid-β Peptides," Nature, 423, pp. 435-439, 2003.

Rask et al., "Wnt-Signaling Pathway in Ovarian Epithelial Tumours: Increased Expression of β-Catenin and GSK3β," Br. J. Cancer, 89(7), pp. 1298-1304, 2003.

Ring et al., Selective Glycogen Synthase Kinase 3 Inhibitors Potentiate Insulin Activation of Glucose Transport and Utilization in Vitro and in Vivo, Diabetes, 52, pp. 588-595, Mar. 2003.

Ross et al., "Glycogen Synthase Kinase 3 Is an Insuling-Regulated C/EBPα Kinase," Molecular and Cellular Biology, 19(12), pp. 8433-8441, Dec. 1999.

Rouse et al., "A Novel Kinase Cascade Triggered by Stress and Heat Shock that Stimulates MAPKAP Kinase-2 and Phosphorylation of the Small Heat Shock Proteins," Cell 78, 1027-1034, Sep. 1994, Abstract only.

Ryu et al., "Endoplasmic Reticulum Stress and the Unfolded Protein Response in Cellular Models of Parkinson's Disease,"J. Neurosci., 22(24), pp. 10690-10698, Dec. 15, 2002.

Schreyer et al., "C57BL/6 Mice Fed High Fat Diets as Models for Diabetes-Accelerated Atherosclerosis," Atherosclerosis 136(1), pp. 17-24, Jan. 1, 1998, Abstract only.

Seger et al., "The MAPK Signaling Cascade," The FASEB Journal, 9, pp. 726-735, 1995.

Shaulian et al., "AP-1 in Cell Proliferation and Survival," Oncogene, 20, pp. 2390-2400, 2001.

Sherman et al., "Cellular Defenses Against Unfolded Proteins: A Cell Biologist Thinks About Neurodegenerative Diseases," Neuron 29, pp. 15-32, Jan. 2001.

Shimura et al., Familial Parkinson Disease Gene Product, Parkin, is a Ubiquitin-protein Ligase, Nat. Genet. 25, pp. 302-305, 2000, Abstract only.

Skorski et al., "Transformation of Hematopoietic Cells by BCR/ABL Requires Activation of a PI-3k/Akt-Dependent Pathway," EMBO J., 16(20), pp. 6151-6161, 1997.

Somervaille et al., "Growth Factor Withdrawal from Primary Human Erythroid Progenitors Induces Apoptosis through a Pathway Involving Glycogen Synthase Kinase-3 and Bax," Blood 98(5), pp. 1374-1381, Sep. 1, 2001.

Song et al., "Central Role of Glycogen Synthase Kinase-3βin Endoplasmic Reticulum Stress-Induced Caspase-3 Activation," J. Biol. Chem., 277(47), pp. 44701-44708, 2002.

Spencer et al., "Conjugates of Catecholamines with Cystein and GSH in Parkinson's Disease : Possible Mechanisms of Formation Involving Reactive Oxygen Species," J. Neurochem. ,71, pp. 2112-2122, 1998.

Surwit et al., "Diet-Induced Type II Diabetes in C57BL/6J Mice," Diabetes 37, pp. 1163-1167, 1988, Abstract only.

Sutherland et al., "Inactivation of Glycogen Synthase Kinase-3β by Phosphorylation: New Kinase Connections in Insulin and Growth-Factor Signaling," Biochem. J. 296, pp. 15-19, 1993.

Tanji et al., "Glycogen Synthase Kinase-3beta Phosphorylates Synphilin-1 in vitro," Neuropathology 23, pp. 199-202, 2003.

Tong et al., "Phosphorylation of Glycogen Synthase Kinase-3β During Preconditioning Through a Phosphatidylinositol-3-Kinase-Dependent Pathway Is Cardioprotective," Circ. Res., 90, pp. 377-379, 2002.

Tong et al., "Activation of Glycogen Synthase Kinase 3 Beta (GSK-3β) by Platelet Activating Factor Mediates Migration and Cell Death in Cerebellar Granule Neurons," Eur. J. Neurosci., 13, pp. 1913-1922, 2001.

Toone et al., "Redox Control of AP-1-Like Factors in Yeast and Beyond," Oncogene, 20, pp. 2336-2346, 2001.

Tsunoda et al., "Two Models for Multiple Sclerosis: Experimental Allergic Encephalomyelitis and Theiler's Murine Encephalomyelitis Virus," J Neuropathol Exp Neurol. 55(6), pp. 673-86, Jun. 1996, Abstract only.

Van Mater et al., "Transient Activation of β-Catenin Signaling in Cutaneous Keratinocytes is Sufficient to Trigger the Active Growth Phase of the Hair Cycle in Mice," Genes Dev., 17, pp. 1219-1224, 2003.

Venkatesan et al., "Insulin Resistance in Polycystic Ovary Syndrome: Progress and Paradoxes," Recent Progress in Hormone Research 56, pp. 295-308, 2001.

Wagman et al., "Discovery and Development of GSK3 Inhibitors for the Treatment of Type 2 Diabetes," Curr. Pharm. Des., 10(10), pp. 1105-1137, 2004.

Werstuck et al., "Homocysteine-Induced Endoplasmic Reticulum Stress Causes Dysregulation of the Cholesterol and Triglyceride Biosynthetic Pathways," J. Clin. Invest., 107(10), pp. 1263-1273, May 2001.

Wickelgren, "Obesity: How Big a Problem?" Science 280(5368), pp. 1364-1367, May 29, 1998, Abstract only.

Wyttenbach et al., "Heat Shock Protein 27 Prevents Cellular Polyglutamine Toxicity and Suppresses the Increase of Reactive Oxygen Species Causes by Huntingtin," Hum. Mol. Genet. 11(9), pp. 1137-1151, 2002.

* cited by examiner

GSK-3 INHIBITORS

This application claims priority as a continuation under 35 U.S.C. §120 from U.S. Ser. No. 11/098,610, filed Apr. 5, 2005, and priority under 35 U.S.C. §119(a)-(d) from EP 04075997.9, filed Apr. 5, 2004. The contents of each of the above-listed applications are incorporated by reference.

FIELD OF THE INVENTION

The present invention relates to enzyme inhibitors, and more particularly to heterocyclic inhibitors of glycogen synthase kinase 3β, GSK-3, to processes of preparation of such compounds, to pharmaceutical compositions comprising them, and to their use for the treatment and or prophylaxis of a disease in which GSK-3 is involved, such as Alzheimer's disease or non-insulin dependent diabetes mellitus.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases. Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes (Coghlan et al., *Chemistry & Biology*, 7, 793-803 (2000); Kim and Kimmel, *Curr. Opinion Genetics Dev.*, 10, 508-514 (2000)). The threonine/serine kinase glycogen synthase kinase-3 (GSK-3) fulfills a pivotal role in various receptor-linked signaling pathways (Doble, B W, Woodgett, J R, *J. Cell Sci.* 2003, 116:1175-1186). Dysregulation within these pathways is considered a crucial event in the development of several prevalent human disorders, such as type II diabetes (Kaidanovich O, Eldar-Finkelman H, *Expert Opin. Ther. Targets*, 2002, 6:555-561), Alzheimer's disease (Grimes C A, Jope R S, *Prog. Neurobiol.* 2001, 65:391-426), CNS disorders such as manic depressive disorder and neurodegenerative diseases, and chronic inflammatory disorders (Hoeflich K P, Luo J, Rubie E A, Tsao M S, Jin O, Woodgett J, *Nature* 2000, 406:86-90). These diseases may be caused by, or result in, the abnormal operation of certain cell signaling pathways in which GSK-3 plays a role.

GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

Currently, inhibition of GSK-3 may represent a viable strategy to develop novel medicinal entities for the treatment of such unmet diseases (Martinez A, Castro A, Dorronsoro 1, Alonso M, *Med. Res. Rev.*, 2002, 22:373-384) through insulin mimicry, tau dephosphorylation and amyloid processing, or transcriptional modulation respectively.

Among the great diversity of chemical structures with GSK-3 inhibition already found (Dorronsoro, 1; Castro, A; Martinez, A *Exp Opin Ther Patents* 2002, 12:1527-1536; Alonso, M. and Martinez, A. *Current Medicinal Chemistry* 2004, 11, 753-761), the 2,4-disubstituted thiadiazolidinone (TDZD) are presented as the first ATP-non competitive GSK-3 inhibitors (Martinez A, Alonso M, Castro A, Perez C, Moreno F, *J Med Chem*, 2002, 45:1292-1299; WO 01 85685 and U.S. 2003/0195238). These compounds have great interest since they are selective and do not show inhibition on other several kinases such as PKA, PKC, CK-2 and CDK1/cyclin B. However, thiadiazolidinones have the tendency to react with nucleophiles and this property may jeopardize their drug potential.

There is still a need to find good GSK-3 inhibitors, being both effective and selective, and having good "drugability" properties, i.e. good pharmaceutical properties related to administration, distribution, metabolism and excretion.

DESCRIPTION OF THE INVENTION

Taking advantage of some of our molecular modeling results and theories, we have designed and synthesized a second generation of 2,4-disubstituted thiadiazolidinones (TDZD) which are very stable against thiol-containing biological molecules such as glutathione and BSA (bovine serum albumin). Surprisingly, these compounds have also a very favorable drugable profile, in particular oral bioavailability and blood brain barrier penetration.

In one aspect the invention is directed to compounds of general formula I:

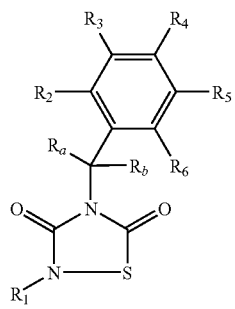

wherein:

$R_1$ is an organic group having at least 8 atoms selected from C or O, which is not linked directly to the N through a —C(O)— and comprising at least an aromatic ring;

$R_a$, $R_b$, $R_2$, $R_3$, $R_4$, $R_5$, $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR$_7$, —C(O)OR$_7$, —C(O)NR$_7$R$_8$ —C=NR$_7$, —CN, —OR$_7$, —OC(O)R$_7$, —S(O)$_t$—R$_7$, —NR$_7$R$_8$, —NR$_7$C(O)R$_8$, —NO$_2$, —N=CR$_7$R$_8$ or halogen, t is 0, 1, 2 or 3, $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen;

wherein $R_a$ and $R_b$ together can form a group =O, and wherein any pair $R_aR_2$, $R_2R_3$, $R_3R_4$, $R_4R_5$, $R_5R_6$, $R_6R_b$, or $R_7R_8$ can form together a cyclic substituent;

or a pharmaceutically acceptable salt, prodrug or solvate thereof.

We have found that compounds with a benzyl like structure at position 4 and a bulky group comprising an aromatic ring or rings at position 2 of the thiadiazolidinones interact optimally with the GSK-3 enzyme while at the same time presenting good drugability properties.

Preferred compounds are those in which $R_1$ has an aromatic group having at least 10 aromatic carbons. These compounds show good activity, stability and reduced binding to plasma proteins like glutathione and albumin.

Also preferred are compounds in which $R_1$ has an aromatic group directly linked to the N of the thiadiazolidine.

In a particular embodiment compounds in which $R_1$ is a naphthyl group are preferred, most preferably if $R_1$ is a α-naphthyl group.

Another preferred class of compounds are those in which the substituent at position 4 of the TDZD is an unsubstituted benzyl group.

In another aspect the invention is directed to pharmaceutical compositions which comprise a compound according to formula (I) or a pharmaceutically acceptable salt, prodrug or solvate thereof, and a pharmaceutically acceptable carrier, adjuvant or vehicle. In a preferred embodiment the formulation is oral.

The present invention is also directed to the use of the above defined compounds in the manufacture of a medicament, preferably for a GSK-3 mediated disease or condition.

Alternatively, the invention is also directed to a method of treatment of a GSK-3 mediated disease or condition comprising the administration of an effective amount of a compound of formula I as defined above, or a pharmaceutically acceptable salt, prodrug or solvate thereof, to a patient in need thereof.

In another aspect, the invention is directed to the use of the above defined compounds as reactives for biological assays, preferably as a reactive for GSK-3 inhibition.

In another aspect the invention is directed to a process for preparing a compound of formula I above by reaction of the appropriate benzyl isothiocyanate with an isocyanate of formula $R_1$—N=C=O.

DETAILED DESCRIPTION OF THE INVENTION

The typical compounds of this invention selectively inhibit GSK-3β without inhibition of other protein kinases such as PKA, PKC, CK-2 and CdK2, which could eliminate the effects. Additionally they do not bind significantly to model proteins such as Glutathione and Bovine Serum Albumin which is a good indication of their stability in plasma. They also show good absorption and blood brain barrier permeability as demonstrated by the examples.

In the above definition of compounds of formula (I) the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as halo, hydroxy, alkoxy, carboxy, cyano, carbonyl, acyl, alkoxycarbonyl, amino, nitro, mercapto and alkylthio.

"Alkoxy" refers to a radical of the formula —ORa where Ra is an alkyl radical as defined above, e.g., methoxy, ethoxy, propoxy, etc.

"Alkoxycarbonyl" refers to a radical of the formula —C(O)ORa where Ra is an alkyl radical as defined above, e.g., methoxycarbonyl, ethoxycarbonyl, propoxycarbonyl, etc.

"Alkylthio" refers to a radical of the formula —SRa where Ra is an alkyl radical as defined above, e.g., methylthio, ethylthio, propylthio, etc.

"Amino" refers to a radical of the formula —NH$_2$, —NHRa or —NRaRb, wherein Ra and Rb are as defined above.

"Aryl" refers to a phenyl, naphthyl, indenyl, fenanthryl or anthracyl radical, preferably phenyl or naphthyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Acyl" refers to a radical of the formula —C(O)—$R_c$ and —C(O)—$R_d$ where $R_c$ is an alkyl radical as defined above and $R_d$ is an aryl radical as defined above, e.g., acetyl, propionyl, benzoyl, and the like.

"Aroylalkyl" refers to an alkyl group substituted with —Ra—C(O)—Rd, wherein Ra is an alkyl radical. Preferred examples include benzoylmethyl.

"Carboxy" refers to a radical of the formula —C(O)OH.

"Cycloalkyl" refers to a stable 3-to-10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more such as alkyl, halo, hydroxy, amino, cyano, nitro, alkoxy, carboxy and alkoxycarbonyl.

"Fused aryl" refers to an aryl group, especially a phenyl or heteroaryl group, fused to another ring.

"Halo" refers to bromo, chloro, iodo or fluoro.

"Haloalkyl" refers to an alkyl radical, as defined above, that is substituted by one or more halo radicals, as defined above, e.g., trifluoromethyl, trichloromethyl, 2,2,2-trifluoroethyl, 1-fluoromethyl-2-fluoroethyl, and the like.

"Heterocycle" refers to a heterocyclyl radical. The heterocycle refers to a stable 3-to-15 membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, derivatives, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluensulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug Design and Discovery" Taylor & Francis (April 2002).

The compounds of the invention may be in crystalline form either as free compounds or as solvates (e.g. hydrates) and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centers or isomers depending on the presence of multiple bonds (e.g. Z, E). The single isomers, enantiomers or diastereoisomers and mixtures thereof fall within the scope of the present invention.

We have found that the compounds of formula I above are selective GSK-3 inhibitors (they do not show inhibition on other kinases) and additionally they present good pharmacological properties which makes them suitable for drug development. Indeed, through the adequate selection of the size and chemical characteristics of the substituents on the TDZD ring we have obtained compounds that are very stable against plasma molecules such as glutathione and BSA, and have shown good oral bioavailability and blood barrier penetration.

In one embodiment, $R_1$ comprises an aromatic group, and this improves the stability properties. In one embodiment, $R_1$ has at least 10 aromatic carbons. Alternatively, good compounds are obtained with electron donating groups on the aromatic ring such as alkoxyl or methylenedioxy.

Although $R_1$ can be linked to the TDZD through any group as long as it is not —C(O)— (because of degradation and poor stability in plasma), it is preferred that the aromatic group is directly linked to the N of the TDZD.

Representative substituents that can be used as $R_1$ are the following:

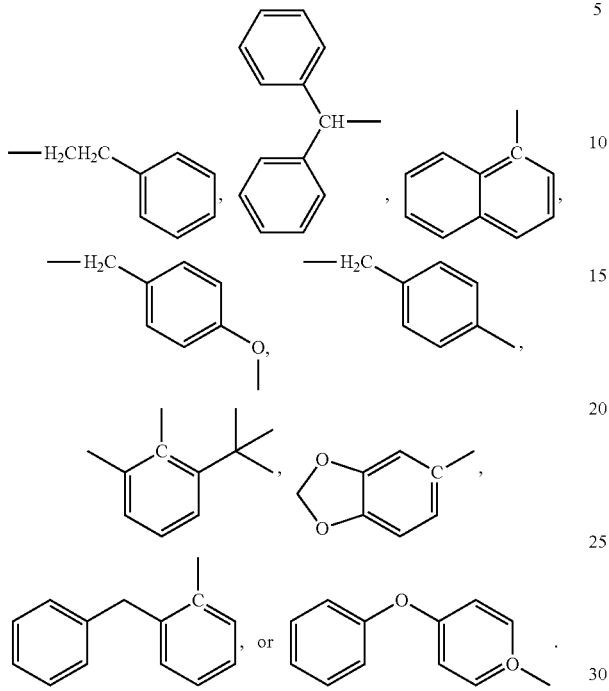

Very good results of stability and bioavailability in vivo have been obtained with a bulky aromatic group such as naphthyl. In particular alpha-naphthyl has given good results. When $R_1$ is alpha-naphthyl, it is preferred that it is an unsubstituted alpha-naphthyl.

Concerning the substituent at position 4 of the TDZD, it is preferred that $R_a$ and $R_b$ are H.

In another embodiment it is preferred that $R_2$, $R_3$, $R_4$, $R_5$, $R_6$ are independently selected from hydrogen, substituted or unsubstituted alkyl, $COR_7$, —$C(O)OR_7$, —$OR_7$, —$NR_7R_8$, or halogen.

Most preferably the substituent at position 4 is unsubstituted benzyl.

Representative compounds of the invention are the following:

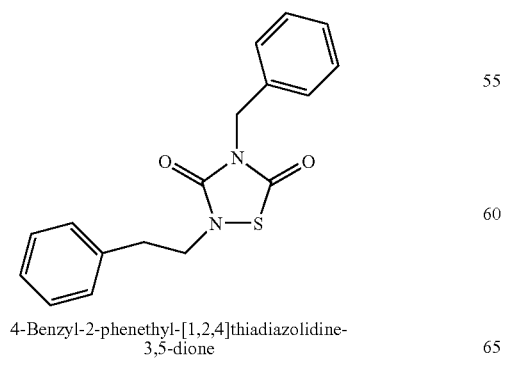

4-Benzyl-2-phenethyl-[1,2,4]thiadiazolidine-3,5-dione

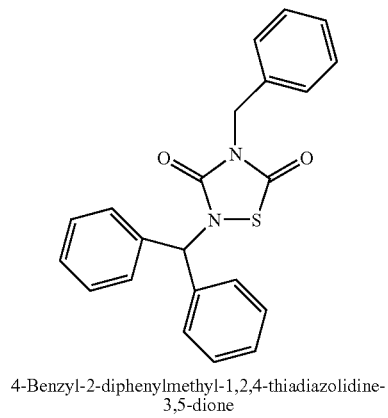

4-Benzyl-2-diphenylmethyl-1,2,4-thiadiazolidine-3,5-dione

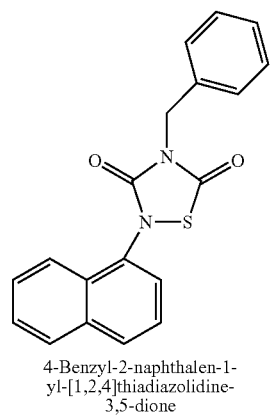

4-Benzyl-2-naphthalen-1-yl-[1,2,4]thiadiazolidine-3,5-dione

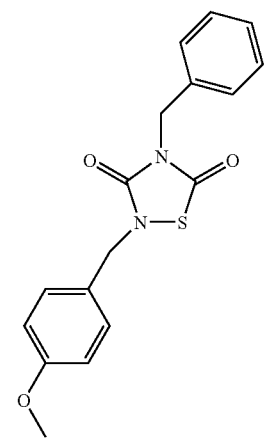

4-Benzyl-2-(4-methoxy-benzyl)-[1,2,4]thiadiazolidine-3,5-dione

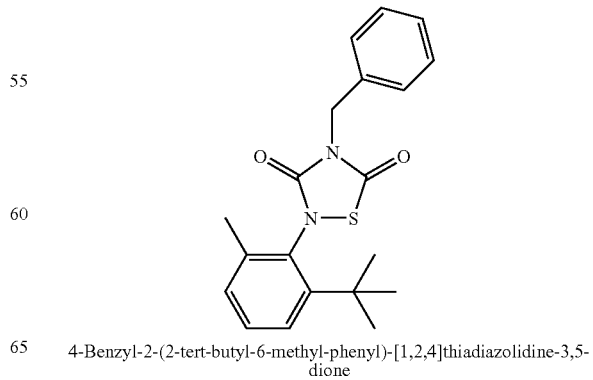

4-Benzyl-2-(2-tert-butyl-6-methyl-phenyl)-[1,2,4]thiadiazolidine-3,5-dione

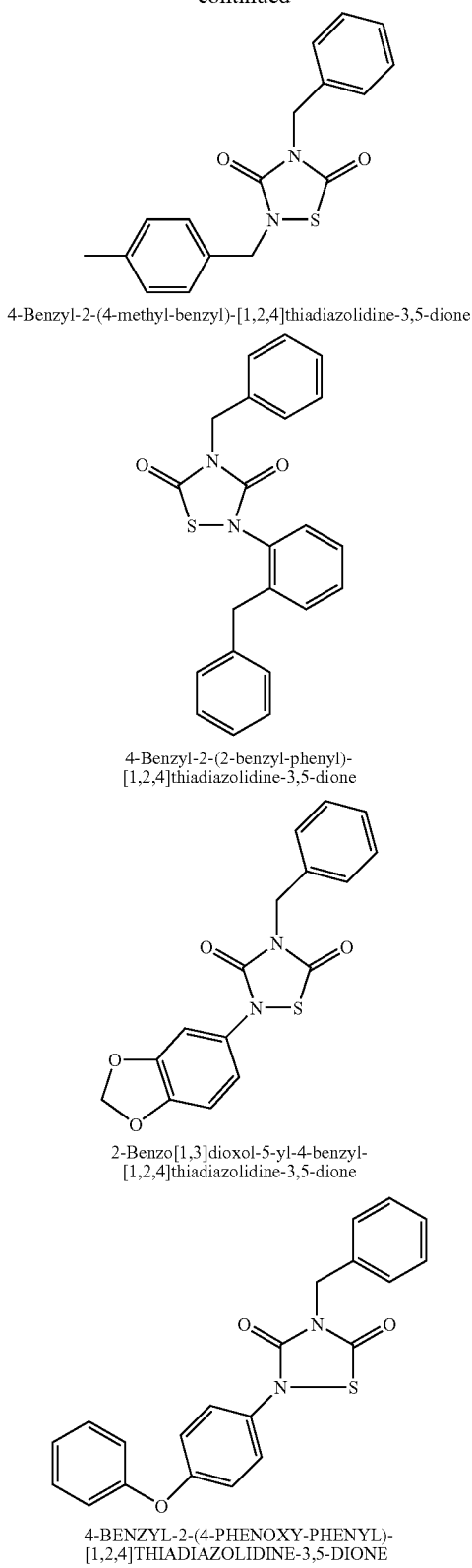

4-Benzyl-2-(4-methyl-benzyl)-[1,2,4]thiadiazolidine-3,5-dione

4-Benzyl-2-(2-benzyl-phenyl)-[1,2,4]thiadiazolidine-3,5-dione

2-Benzo[1,3]dioxol-5-yl-4-benzyl-[1,2,4]thiadiazolidine-3,5-dione

4-BENZYL-2-(4-PHENOXY-PHENYL)-[1,2,4]THIADIAZOLIDINE-3,5-DIONE and their salts, prodrugs and solvates.

The compounds of formula (I) defined above can be obtained by available synthetic procedures. Some examples of these procedures are described in WO 01/85685 and US 2003/0195238 and references therein. The content of these documents is incorporated herein by reference in its entirety.

Therefore in another aspect the invention provides a process for the preparation of a compound of formula (I) or a salt or solvate thereof as described herein, which comprises reacting a benzyl substituted isothiocyanate of formula II

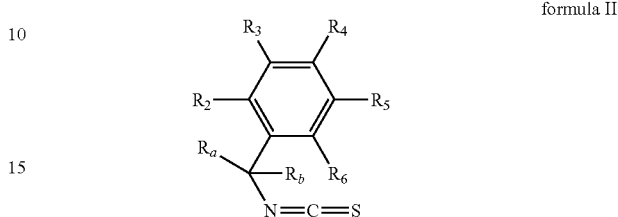

formula II with a compound of formula $R_1$—N=C=O.

For example, the following procedure can be used to produce 4-N-benzyl substituted thiadiazolidinones:

Scheme 1

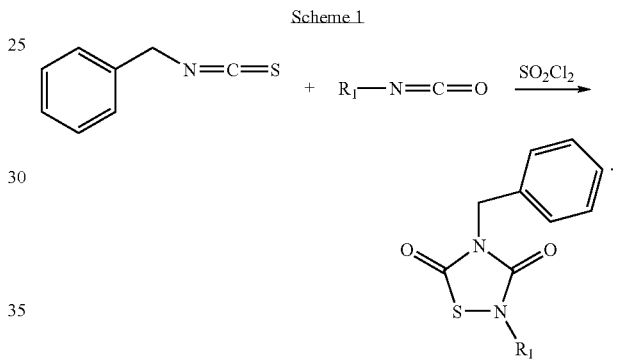

The general experimental procedure of Scheme 1 is described for example in Slomczynska, U.; Barany, G., "Efficient Synthesis of 1,2,4-Dithiazolidine-3,5-diones (Dithiasuccinoylamines) and observations on formation of 1,2,4-Thiadiazolidine-3,5-dione by related Chemistry", *J. Heterocyclic Chem.*, 1984, 21, 241-246.

For example, sulfuryl chloride is added dropwise with stirring, under nitrogen atmosphere, preferably at low temperature, preferably at about 5° C., to a solution of benzyl isothiocyanate and the isocyanate indicated in each case, in a suitable solvent such as hexane, ether or THF. When the addition is finished, the mixture is left to react, for example by stirring for 20 hours at room temperature. After this time, the resulting product is isolated by conventional methods such as suction filtration or solvent evaporation and then, the purification is performed (e.g. by recrystallization or silica gel column chromatography using the appropriate eluent).

Other alternative procedures will be apparent to the person skilled in the art, such as the use of any other chlorinating agent instead of sulfuryl chloride, variations in the order of addition of the reactants and reaction conditions (solvents, temperature, etc).

The reaction products may, if desired, be purified by conventional methods, such as crystallization, chromatography and trituration.

One preferred pharmaceutically acceptable form is the crystalline form, including such form in a pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing a GSK-3 mediated disease with a GSK-3 inhibitor as described above, which method comprises administering to a patient in need of such a treatment a therapeutically effective amount of a compound of formula (I) or a pharmaceutical composition thereof.

The terms "GSK-3 mediated disease, or "GSK-3 mediated condition", as used herein, mean any disease or other deleterious condition or state in which GSK-3 is known to play a role. Such diseases or conditions include, without limitation, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, brain injury, especially traumatic brain injury, cancer, leukopenia, Down's syndrome, Lewy body disease, inflammation, chronic inflammatory diseases, cancer and hyperproliferative diseases as hyperplasias and immunodeficiency.

In a particular embodiment of the invention the compounds of formula (I) or their pharmaceutical compositions, e.g. in oral form, are used for the treatment of Alzheimer's disease.

In another embodiment of the invention the compounds of formula (I) or their pharmaceutical compositions, e.g. in oral form, are used for the treatment of diabetes.

In another embodiment of the invention the compounds of formula (I) or their pharmaceutical compositions, e.g. in oral form, are used for the treatment of depression.

In another embodiment of the invention the compounds of formula (I) or their pharmaceutical compositions, e.g. in oral form, are used for the treatment of brain injury.

The present invention further provides pharmaceutical compositions comprising a compound of this invention, pharmaceutically acceptable salts, derivatives, prodrugs or stereoisomers thereof with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form. Suitable dose forms for oral administration may be tablets and capsules and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of many of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

In another aspect the invention relates to inhibiting GSK-3 activity in a biological sample with the compounds of formula (I), which method comprises contacting the biological sample with a GSK-3 inhibitor of formula (I). The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof. Thus, in one aspect the invention is directed to the use of compounds of formula I as reactives for biological assays, in particular as a reactive for GSK-3 inhibition.

The following examples are intended to further illustrate the invention. They should not be interpreted as a limitation of the scope of the invention as defined in the claims.

EXAMPLES

Synthesis of Compounds

General Experimental Procedure:
Sulfuryl chloride is added dropwise with stirring, under nitrogen atmosphere, at 5° C. to a solution of benzyl isothiocyanate and the isocyanate indicated in each case, in hexane, ether or THF. When the addition is finished, the mixture is stirred for 20 hours at room temperature. After this time, the resulting product is isolated by suction filtration or by solvent evaporation and then, the purification is performed by recrystallization or silica gel column chromatography using the appropriate eluent. More details can be found in Slomczynska, U.; Barany, G., "Efficient Synthesis of 1,2,4-Dithiazolidine-3,5-diones (Dithiasuccinoyl-amines) and observations on formation of 1,2,4-Thiadiazolidine-3,5-dione by related Chemistry", *J. Heterocyclic Chem.*, 1984, 21, 241-246.

Example 1

2-Phenethyl-4-benzyl-(1,2,4)thiadiazolidine-3,5-dione (1)

Reagents: Benzyl-isothiocyanate (6.5 mmol, 0.85 mL), phenethylisocyanate (6.5 mmol, 0.89 mL) and $SO_2Cl_2$ (6.5 mmol, 0.52 mL) in diethyl ether (25 mL). Isolation: solvent evaporation. Purification: silica gel column chromatography (AcOEt/hexane, 1:4).

Yield: 1.5 g (74%), yellow oil.

$^1$H-NMR (CDCl$_3$): 2.9 (t, 2H, CH$_2$CH$_2$Ph, J=7.2 Hz); 3.9 (t, 2H, CH$_2$CH$_2$Ph, J=7.2 Hz); 4.8 (s, 2H, CH$_2$Ph); 7.2-7.4 (m, 10H, arom)

$^{13}$C-NMR (CDCl$_3$): 34.9 (CH$_2$CH$_2$Ph); 4.9 (CH$_2$CH$_2$Ph); 46.2 (CH$_2$Ph); 126.9; 128.5; 128.6; 136.6 (C arom CH$_2$Ph); 128.1; 128.6; 128.6; 135.0 (C arom CH$_2$CH$_2$Ph); 152.6 (3-C=O); 165.6 (5-C=O).

Anal (C$_{17}$H$_{16}$N$_2$O$_2$S), C, H, N, S.

Example 2

4-Benzyl-2-naphthalen-1-yl-[1,2,4]thiadiazolidine-3,5-dione (2)

Reagents: Benzyl-isothiocyanate (13 mmol, 1.72 mL), 1-naphthyl-isocyanate (13 mmol, 1.9 mL) and $SO_2Cl_2$ (13 mmol, 1.04 mL) in hexane (50 mL). Isolation: filtration of reaction mixture.

Purification: recrystallization from EtOH.

Yield: 3.8 g (87%), white needles. mp=150° C.

$^1$H-NMR (CDCl$_3$): 4.9 (s, 2H, CH$_2$Ph); 7.3-7.9 (m, 12H, arom.)

$^{13}$C-NMR (CDCl$_3$): 46.5 (CH$_2$Ph); 128.3; 128.6; 129.0; 135.0 (C arom, Ph); 122.0; 125.3; 126.8; 127.2; 127.5; 128.5; 130.8; 134.4 (C arom, naphthyl); 152.2 (3-C=O); 165.9 (5-C=O).

Anal (C$_{19}$H$_{14}$N$_2$O$_2$S), C, H, N, S.

Example 3 (Comparative)

2-(1-adamantyl)-4-benzyl-[1,2,4]thiadiazolidine-3,5-dione (3)

Reagents: Benzylisothiocyanate (6.5 mmol, 0.85 mL), 1-Adamantyl-isocyanate (6.5 mmol, 1.15 g) and $SO_2Cl_2$ (6.5 mmol, 0.52 mL) in diethyl ether (25 mL). Isolation: solvent evaporation.

Purification: silica gel column chromatography (AcOEt/hexane, 1:4).

Yield: 0.89 g (40%), yellow crystals. mp=128.8° C.

$^1$H-NMR (CDCl$_3$): 1.7 (m, 6H, adamantyl); 2.2 (m, 3H, adamantyl); 2.3 (m, 6H, adamantyl); 4.8 (s, 2H, CH$_2$Ph); 7.2-7.4 (m, 5H, arom)

$^{13}$C-NMR (CDCl$_3$): 29.9; 30.0; 35.9; 41.0; 60.0 (C adamantyl); 45.3 (CH$_2$Ph); 127.8; 128.5; 128.6; 135.4 (C arom).

Anal. (C$_{19}$H$_{22}$N$_2$O$_2$S), C, H, N, S.

Example 4

4-Benzyl-2-(4-methyl-benzyl)-[1,2,4]thiadiazolidine-3,5-dione (4)

Reagents: Benzylisothiocyanate (6.5 mmol, 0.85 mL), 4-methylbenzyl-isocyanate (6.5 mmol, 0.90 mL) and $SO_2Cl_2$ (6.5 mmol, 0.52 mL) in diethyl ether (25 mL). Isolation: filtration of reaction mixture. Purification: recrystallization from MeOH.

Yield: 0.95 g (48%), white solid. mp=69.1° C.

$^1$H-NMR (CDCl$_3$): 2.4 (s, 3H, CH$_3$); 4.7 (s, 2H, CH$_2$-Ph); 4.8 (2H, s, CH$_2$-Ph); 7.2 (s, 4H, arom); 7.2-7.5 (m, 5H, arom).

$^{13}$C-NMR (CDCl$_3$): 21.3 (CH$_3$); 45.9 (CH$_2$Ph); 48.5 (CH$_2$Ph); 128.1; 128.6; 128.7; 135.0 (C arom); 128.4; 129.5; 131.1; 138.6 (C arom); 152.8 (3-C=O); 165.7 (5-C=O).

Anal. (C$_{17}$H$_{16}$N$_2$O$_2$S), C, H, N, S.

Example 5

4-Benzyl 2-((3,4-methylenedioxy)phenyl)-[1,2,4]thiadiazolidine-3,5-dione (5)

Reagents: Benzylisothiocyanate (6.5 mmol, 0.85 mL), 3,4-(methylenedioxy)phenyl-isocyanate (6.5 mmol, 1.06 mL) and $SO_2Cl_2$ (6.5 mmol, 0.52 mL) in diethyl ether (25 mL). Isolation: filtration of reaction mixture. Purification: recrystallization from MeOH.

Yield: 1.4 g (66%), white solid. mp=126.5° C.

$^1$H-NMR (CDCl$_3$): 4.9 (s, 2H, CH$_2$Ph); 6.0 (s, 2H, O—CH$_2$—O); 6.7-7.0 (m, 3H, arom); 7.3-7.5 (m, 5H, arom)

$^{13}$C-NMR (CDCl$_3$): 46.2 (CH$_2$Ph); 128.2; 128.6; 129.0; 134.9 (C arom); 101.8 (O—CH$_2$—O); 106.4; 108.3; 118.2; 129.0; 148.1; 146.8 (Carom); 151.2 (3-C=O); 164.9 (5-C=O)

Anal. (C$_{16}$H$_{12}$N$_2$O$_4$S), C, H, N, S.

Example 6

4-Benzyl-2-diphenylmethyl-1,2,4-thiadiazolidine-3,5-dione (6)

Reagents: Benzylisothiocyanate (6.5 mmol, 0.85 mL), diphenylmethyl-isocyanate (6.5 mmol, 1.23 mL) and $SO_2Cl_2$ (6.5 mmol, 0.52 mL) in diethyl ether (25 mL). Isolation: filtration of reaction mixture. Purification: recrystallization from MeOH.

Yield: 1.79 g (80%), white solid. mp=111.5° C.

$^1$H-NMR (CDCl$_3$): 4.85 (s, 2H, CH$_2$Ph); 6.8 (s, 1H, Ph-CH-Ph); 7.2-7.4 (m, 15H, arom)

$^{13}$C-NMR (CDCl$_3$): 45.9 (CH$_2$Ph); 61.6 (Ph-CH-Ph); 128.0; 128.6; 128.7; 135.0 (C arom); 128.1; 128.5; 128.5; 137.5 (2×Ph); 152.6 (3-C=O); 165.8 (5-C=O) Anal. (C$_{22}$H$_{18}$N$_2$O$_2$S), C, H, N, S.

Example 7

4-Benzyl-2-(4-methoxybenzyl)-[1,2,4]thiadiazolidine-3,5-dione (7)

Reagents: Benzylisothiocyanate (6.5 mmol, 0.85 mL), p-methoxybenzyl-isocyanate (6.5 mmol, 0.92 mL) and $SO_2Cl_2$ (6.5 mmol, 0.52 mL) in diethyl ether (25 mL). Isolation: solvent evaporation. Purification: silica gel column chromatography (AcOEt/hexane, 1:4).

Yield: 1.30 g (61%), yellowish solid. mp=86.4° C.

$^1$H-NMR (CDCl$_3$): 3.8 (s, 3H, CH$_3$); 4.7 (s, 2H, CH$_2$-Ph-OMe); 4.8 (s, 2H, CH$_2$-Ph); 7.2-7.4 (m, 5H, arom); 6.8 (d, 2H, J=8.6 Hz); 7.2 (d, 2H, J=8.6 Hz)(Arom)

$^{13}$C-NMR (CDCl$_3$): 45.9 (CH$_2$-Ph); 48.2 (CH$_2$-Ph-OMe); 55.2 (O—CH$_3$); 128.0; 129.8; 128.4; 135.0 (C arom-Ph); 126.2; 128.5; 114.2; 159.7 (C arom Ph-OMe); 152.7 (3-C=O); 165.6 (5-C=O).

Anal. (C$_{17}$H$_{13}$N$_2$O$_3$S), C, H, N, S.

Example 8

4-Benzyl-2-(2-tert-butyl-6-methyl-phenyl)-(1,2,4)thiadiazolidine-3,5-dione (8)

Reagents: Benzylisothiocyanate (3.5 mmol, 0.45 mL), 2-tert-butyl-6-methylisocyanate (3.5 mmol, 662.5 mg) and $SO_2Cl_2$ (3.5 mmol, 0.25 mL) in diethyl ether (15 mL). Isolation: solvent evaporation. Purification: silica gel column chromatography (AcOEt/hexane, 1:10). Yield: 0.17 g (14%), brown solid. mp=89.8° C.

$^1$H-NMR (CDCl$_3$): 1.4 (s, 9H, C(CH$_3$)$_3$); 2.1 (s, 3H, CH$_3$); 4.9 (2d, 2H, CH$_2$-Ph, J=6.3 Hz); 7.1-7.5 (m, 8H, arom)
$^{13}$C-NMR (CDCl$_3$): 17.8 (CH$_3$); 31.9 (C(CH$_3$)); 35.9 (C(CH$_3$)); 46.2 (CH$_2$-Ph); 126.1; 128.6; 128.5; 135.1 (C arom-Bn); 131.5; 150.4; 139.4; 128.1; 129.5; 129.9 (C arom-Ph); 152.4 (3-C=O); 165.7 (5-C=O)
Anal. (C$_{20}$H$_{22}$N$_2$O$_2$S), C, H, N, S.

Example 9

4-Benzyl-2-(2-benzyl-phenyl)-[1,2,4]thiadiazolidine-3,5-dione (9)

Reagents: Benzylisothiocyanate (6.5 mmol, 0.85 mL), 2-benzylphenyl-isocyanate (6.5 mmol, 0.82 mL) and $SO_2Cl_2$ (6.5 mmol, 0.5 mL) in diethyl ether (25 mL). Isolation: filtration of reaction mixture. Purification: recrystallization from EtOH Yield: 1.50 g (62%), white solid. mp=154.9° C.
$^1$H-NMR (CDCl$_3$): 3.9 (s, 2H, Ph-CH$_2$-Ph); 4.86 (s, 2H, CH$_2$Ph); 6.9-7.5 (m, 14H, arom)
$^{13}$C-NMR (CDCl$_3$): 38.1 (Ph-CH$_2$-Ph); 46.1 (CH$_2$-Ph); 135.1; 128.5; 128.6; 129.2 (C-Bn); 138.9; 129.9; 131.6; 128.4; 127.9; 133.1 (Ph-CH$_2$-Ph); 140.9; 128.7; 128.6; 126.4 (Ph-CH$_2$-Ph); 151.2 (3-C=O); 166.0 (5-C=O)
Anal. (C$_{22}$H$_{18}$N$_2$O$_2$S), C, H, N, S.

Example 10

4-Benzyl-2-(4-phenoxyphenyl)-[1,2,4]thiadiazolidine-3,5-dione (10)

Reagents: Benzylisothiocyanate (13 mmol, 1.6 mL), 4-phenoxyphenyl-isocyanate (13 mmol, 2.3 mL) and $SO_2Cl_2$ (13 mmol, 1 mL) in diethyl ether (50 mL). Isolation: filtration of reaction mixture. Purification: recrystallization from EtOH.

Yield: 4.12 g (84%), white solid. mp=88.8° C.
$^1$H-NMR (CDCl$_3$): 4.92 (s, 2H, CH$_2$Ph); 7.0-7.6 (m, 14H, arom)
$^{13}$C-NMR (CDCl$_3$): 46.1 (CH$_2$Ph); 134.9; 128.7; 129.1; 128.3 (CH$_2$-Ph); 130.1; 125.7; 119.2; 156.3 (Ph-O-Ph); 156.3; 119.1; 129.8; 123.8 (Ph-O-Ph); 151.1 (3-C=O); 165.0 (5-C=O) Anal. (C$_{21}$H$_{16}$N$_2$O$_3$S), C, H, N, S.

Biological Methods

Example 11

GSK-3β Inhibition

The GSK-3β activity was determined by incubation of a mixture of recombinant human GSK-3 enzyme, a phosphate source and GSK-3 substrate in the presence and in the absence of the corresponding test compound, and by measuring the GSK-3 activity of this mixture.

Recombinant human glycogen synthase kinase 3β was assayed in MOPS 8 mM pH 7.3, EDTA 0.2 mM, MgCl$_2$ 10 mM and sodium orthovanadate 0.25 mM in the presence of 62.5 μM of Phospho-Glycogen Synthase Peptide-2 (GS-2), 0.5 μCi γ-$^{33}$P-ATP and unlabelled ATP at a final concentration of 12.5 μM. The final assay volume was 20 μl. After incubation for 30 minutes at 30° C., 15 μl aliquots were spotted onto P81 phosphocellulose papers. Filters were washed four times for at least 10 minutes each and counted with 1.5 ml of scintillation cocktail in a scintillation counter.

The compounds IC$_{50}$ values were calculated analyzing inhibition curves by non-linear regression using GraphPad Prism.

The IC$_{50}$ (concentration at which 50% of enzyme inhibition is shown) values are gathered in table 1.

TABLE I

IC$_{50}$ values

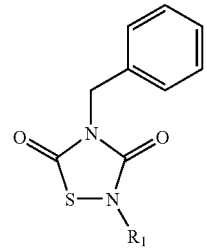

| Comp. | R$_1$ | IC$_{50}$ GSK-3 (μm) |
|---|---|---|
| 1 | 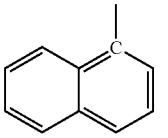 | 3 |
| 2 | 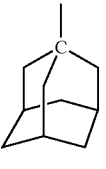 | 2.4 |
| 3 (comparative) | 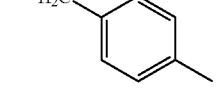 | >50 |
| 4 | 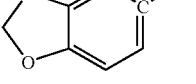 | 1.8 |
| 5 |  | 4.2 |

TABLE I-continued

IC$_{50}$ values

[Structure: 2-R$_1$-1,2,4-thiadiazolidine-3,5-dione with N4-benzyl substituent]

| Comp. | R$_1$ | IC$_{50}$ GSK-3 (μm) |
|---|---|---|
| 6 | diphenylmethyl (CH(Ph)$_2$) | 2 |
| 7 | –H$_2$C–(4-methoxyphenyl) | <50 |
| 8 | 2-methyl-6-tert-butylphenyl | 3 |
| 9 | 2-(iodo)benzyl-phenyl | 8 |
| 10 | 4-phenoxyphenyl | 3 |

Example 12

Binding to GSH and BSA

Sample Preparation

The compounds (working solution at 1 mM) were incubated during 30 minutes at room temperature with Glutathione (Sigma) and Bovine serum albumin (Fraction V) (Sigma) at equimolecular concentrations (1 mM). After this time the solution was filtrated and analysed by HPLC-UV/MS.

Chromatographic Methods

HPLC was performed with a symmetry C18 (2.1×150 mm, 3.5 μm) column using a Waters Alliance 2695 with a 2996 photodiode array and ZQ2000 mass spectrometer used for the analytical separation and for UV and mass determination. The gradient used for the elution was:

| TIME (MIN) | % A | % B |
|---|---|---|
| 0 | 100 | 0 |
| 20 | 0 | 100 |
| 21 | 100 | 0 |
| 25 | 100 | 0 |

Flux: 0.25 mL/min; temp: 30° C.; Detection: 250 nm; Injection Volume: 10 μL

Results are collected in Table 2

TABLE 2

| Compound | % UNBINDING COMPOUND | |
|---|---|---|
|  | GLUTATHIONE | ALBUMIN |
| 1 | 34.7 | 80.2 |
| 2 | 95.0 | 98.0 |
| 3 (COMPARATIVE) | 15.0 | 54.0 |
| 4 | 32.3 | 67.2 |
| 5 | 72.0 | 65.5 |
| 6 | 52.0 | 84.0 |
| 7 | 31.0 | 68.3 |
| 8 | 59.4 | 62.3 |
| 9 | 71.7 | 91.4 |
| 10 | 100.0 | 98.9 |

The table clearly indicates that all the compounds except compound 3 which has no aromatic ring have at least in one of the two properties assayed more than 50% of unbinding compound. There are also some compounds with more than 70% of unbinding compounds in the two assays. The presence of an aromatic group at position 2 (R$_1$) of the TDZD clearly improves the properties of these compounds. This effect is bigger if there are at least 10 aromatic carbons present in the substituent, or electron-donating substituents such as in compounds 5 and 10. We can also observe that when the aromatic group is directly linked to the N of the TDZD the results are better. Best results were obtained with phenyloxyphenyl and with alpha-naphthyl.

These data are clearly better than those of previous TDZD compounds. Indeed, previously described 2,4-dibenzyl-1,2,4-thiadiazolidine-3,5-dione with a smaller substituent at position 2 of the thiadiazolidinone gives a value of 17.1% in the glutathione assay and 57.0% in the albumin assay, much lower than for example present compound 4 which has an additional methyl group, and in the range of comparative example 3 which has no aromatic rings. And the compound with R$_1$=benzoyl decomposes during the assays thus performing much worse than the compounds of formula I.

Example 13

Brain Permeation after Oral and Intravenous Administration

This study was conducted at CIDA S.A.L., Sta Perpetua de Mogola (Barcelona) Spain.

The objective of this study was to investigate the pharmacokinetic behavior of compound 2 (R$_1$=alpha-naphthyl) and its possible accumulation in the brain tissue after both oral and intravenous administration.

C57/BL6 mice (15-30 g) from Charles River laboratories Spain were used in this study. All the mice had free access to the dried, pelleted standard mouse diet. Water was available ad libitum. Animals were fasted for 4 hours before treatment, but with water ad libitum. They were fed 2 hours after administration.

Compound 2 was formulated in 10.0% PEG400, 10.0% Cremophor in bidistilled water. The route of administration was a single oral administration at 20 g/kg (10 mL/kg) and single intravenous administration at 2 mg/kg (10 mL/kg). An additional experiment was performed at 200 mg/kg by the oral route only to determine proportionality of absorption.

Four animals (2 males and 2 females) were used at each extraction time. Blood was heparinized, and after centrifugation (3000 rpm, 10 mins, 5° C.), two plasma aliquots stored at −20° C. and −30° C. until analysis (HPLC/MS-MS).

The summary of the experiment results is showed in the table 3.

TABLE 3

| Dose | 200 mg/kg | 20 mg/kg |
|---|---|---|
| C max | 9061.34 ng/mL | 904.95 ng/mL |
| Bioavailability | Not evaluated | 31.87% |

Compound 2 is quickly absorbed from the GI tract after oral administration. A half-life of 6 hours was found after an oral administration of 20 mg/kg. Compound 2 presented a bioavailability of 31.87%. Levels of Compound 2 were detected in the brain, both after oral and intravenous administration. This shows that compounds of formula I above have good bioavailability properties and are suitable for development as a drug for the treatment of GSK-3 mediated diseases or conditions.

The invention claimed is:

1. A method of treating a GSK-3 mediated disease or condition selected from the group consisting of amyotrophic lateral sclerosis, multiple sclerosis, Parkinson's disease, progressive supranuclear palsy, subacute sclerosing panencephalitic parkinsonism, postencephalitic parkinsonism, pugilistic encephalitis, corticobasal degeneration, Huntington's disease, frontotemporal dementia, guam parkinsonism-dementia complex, Pick's disease, or AIDS associated dementia, in a patient in need thereof, the method comprising administering to said patient a compound according to formula (I) or a pharmaceutical composition comprising a pharmaceutically acceptable carrier, adjuvant, or vehicle, and a compound according to formula (I)

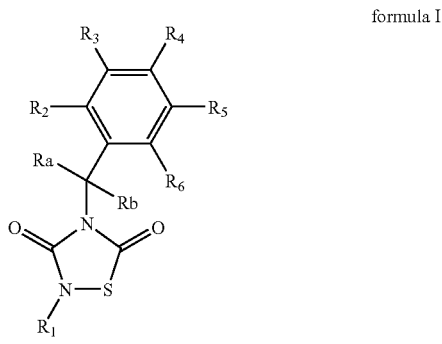

formula I or a pharmaceutically acceptable salt or prodrug thereof;

wherein:

$R_1$ is a group selected from the group consisting of:

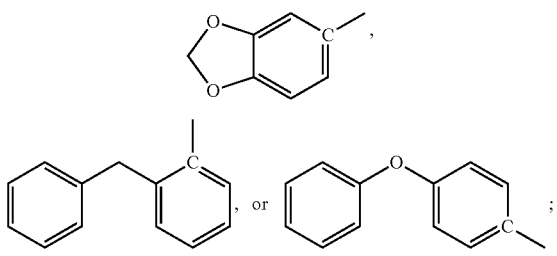

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_7$, —$C(O)OR_7$, —$C(O)NR_7R_8$, —$C=NR_7$, —CN, —$OR_7$, —$OC(O)R_7$, —$S(O)_t$—$R_7$, —$NR_7R_8$, —$NR_7C(O)R_8$, —$NO_2$, —$N=CR_7R_8$ or halogen;

t is 0, 1, 2 or 3; and $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted substituted or unsubstituted aryloxy, or halogen.

2. The method according to claim 1, wherein both $R_a$ and $R_b$ are H.

3. The method according to claim 1, wherein $R_2$, $R_3$, $R_4$, $R_5$, and $R_6$ are independently selected from hydrogen, substituted or unsubstituted alkyl, —$COR_7$, —$C(O)OR_7$, —$OR_7$, —$NR_7R_8$, or halogen, and wherein $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

4. The method according to claim 1, wherein $R_2$, $R_3$, $R_4$, $R_5$, and $R_6$ area H.

5. The method according to claim 1, wherein the compound of formula (I) is selected from the group consisting of

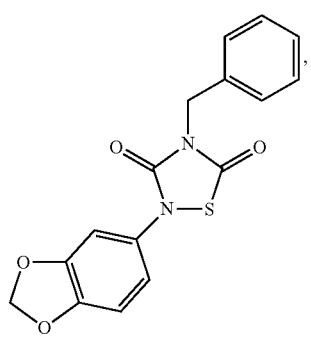

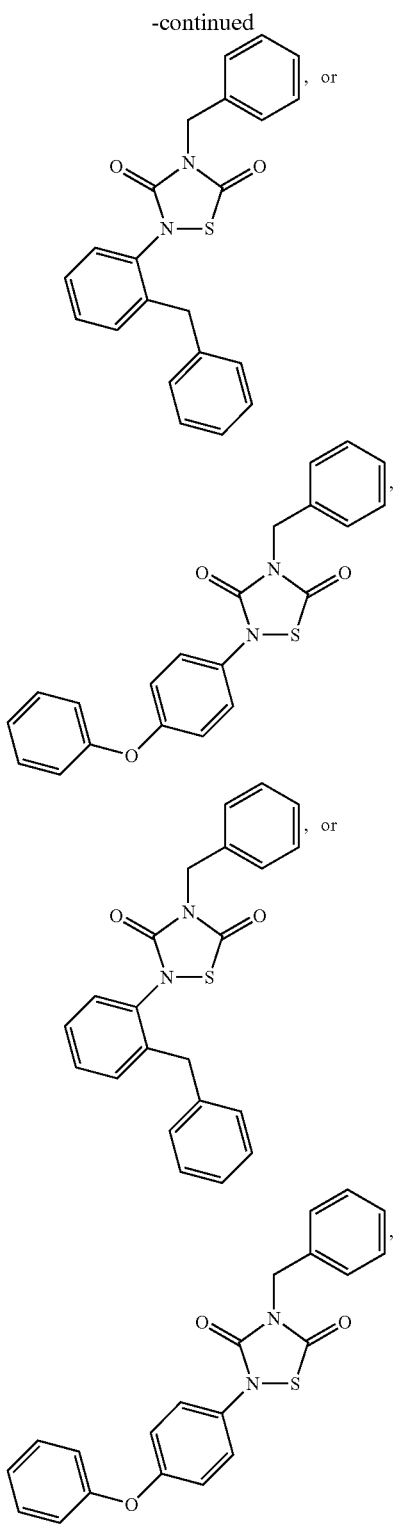

or a pharmaceutically acceptable salt or prodrug thereof.

6. The method according to any one of claims 1 to 5, wherein the disease or condition is selected from the group consisting of amyotrophic lateral sclerosis, or multiple sclerosis.

7. The method according to claims 1 to 5, wherein the disease or condition is selected from the group consisting of Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease or AIDS associated dementia.

8. The method according to claim 7, wherein the disease or condition is progressive supranuclear palsy.

9. A method of treating a GSK-3 mediated disease or condition, selected from neurotraumatic diseases, epilepsy and mood disorders, in a patient in need thereof the method comprising administering to said patient a compound according to formula (I) or a pharmaceutical composition comprising a pharmaceutically acceptable carrier, adjuvant, or vehicle, and a compound according to formula (I)

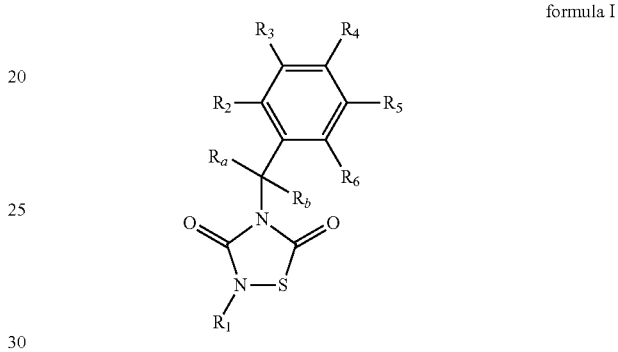

formula I or a pharmaceutically acceptable salt or prodrug thereof; wherein:

$R_1$ is a group selected from the group consisting of

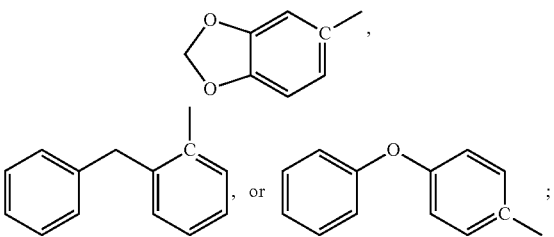

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_7$, —$C(O)OR_7$, —$C(O)NR_7R_8$, —$C=N_7$, —CN, —$OR_7$, —$OC(O)R_7$, —$S(O)_t$—$R_7$, —$NR_7R_8$, —$NR_7C(O)R_8$, —$NO_2$, —$N=CR_7R_8$ or halogen;

t is 0, 1, 2 or 3; and $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

10. The method according to claim 9, wherein both $R_a$ and $R_b$ are H.

11. The method according to claim 9, wherein $R_2$, $R_3$, $R_4$, $R_5$, and $R_6$ are independently selected from hydrogen, substituted or unsubstituted alkyl, —$COR_7$, —$C(O)OR_7$, —$OR_7$, —$NR_7R_8$, or halogen, and wherein $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

12. The method according to claim 9, wherein $R_2$, $R_3$, $R_4$, $R_5$, and $R_6$ are H.

13. The method according to claim 9, wherein the compound of formula (I) is selected from the group consisting of

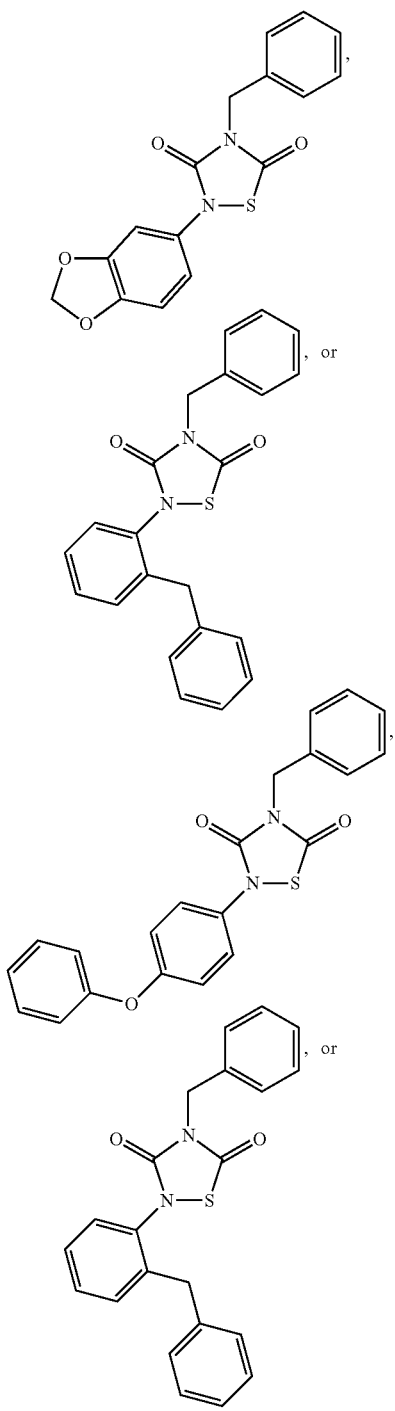

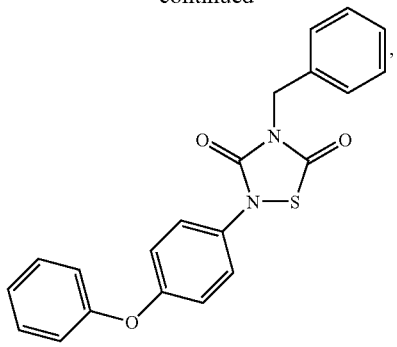

or a pharmaceutically acceptable salt or prodrug thereof.

14. The method according to claim 9, wherein the neurotraumatic disease is acute stroke.

15. The method according to claim 9, wherein the mood disorder is selected from depression, schizophrenia and bipolar disorders.

16. A method of treating a GSK-3 mediated disease or condition which is selected from promotion of functional recovery post stroke, cerebral bleeding, hair loss, obesity, polycystic ovary syndrome, syndrome X, ischaemia, brain injury, leukopenia, Down's syndrome, Lewy body disease, inflammation, and immunodeficiency, in a patient in need thereof, the method comprising administering to said patient a compound according to formula (I) or a pharmaceutical composition comprising a pharmaceutically acceptable carrier, adjuvant, or vehicle, and a compound according to formula (I)

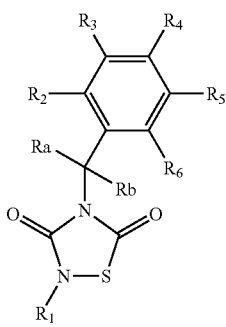

formula I or a pharmaceutically acceptable salt or prodrug thereof; wherein:

$R_1$ is a group selected from the group consisting of:

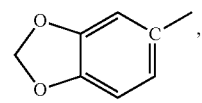

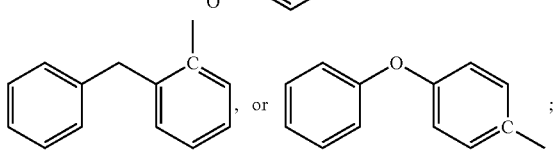

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR₇, —C(O)OR₇, —C(O)NR₇R₈, —C≡N₇, —CN, —OR₇, —OC(O)R₇, —S(O)ₜ—R₇, —NR₇R₈, —NR₇C(O)R₈, —NO₂, —N═CR₇R₈ or halogen;

t is 0, 1, 2 or 3; and

R₇ and R₈ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

17. The method according to claim 16, wherein both R_a and R_b are H.

18. The method according to claim 16, wherein R₂, R₃, R₄, R₅, and R₆ are independently selected from hydrogen, substituted or unsubstituted alkyl, —COR₇, —C(O)OR₇, —OR₇, —NR₇R₈, or halogen, and wherein R₇ and R₈ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

19. The method according to claim 16, wherein R₂, R₃, R₄, R₅, and R₆ are H.

20. The method according to claim 16, wherein the compound of formula (I) is selected from the group consisting of

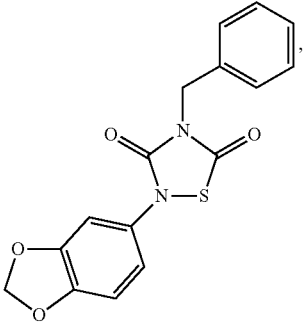,

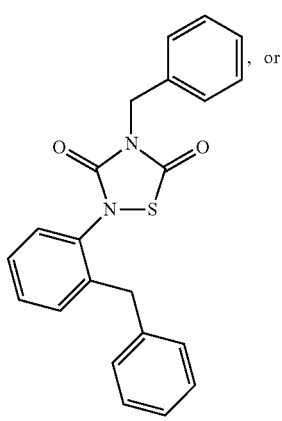, or

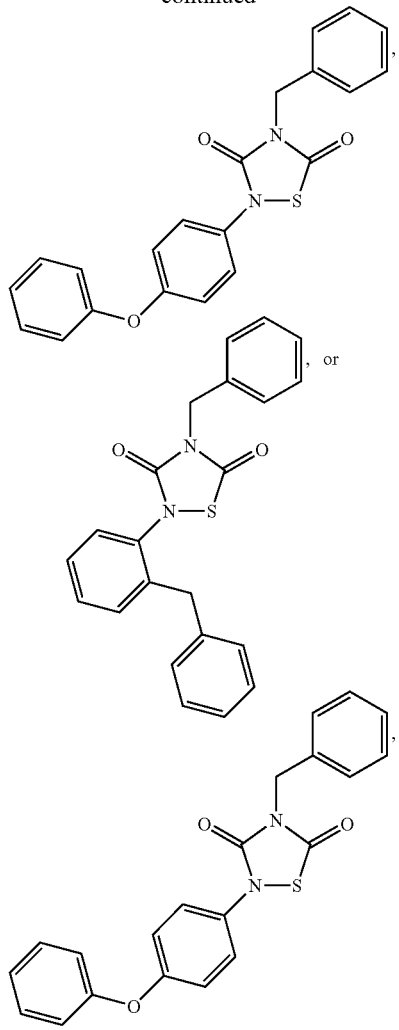

or a pharmaceutically acceptable salt or prodrug thereof.

21. The method according to claim 16, wherein inflammation is a chronic inflammatory disease.

22. The method according to claim 16, wherein brain injury is traumatic brain injury.

23. A method of performing a biological assay for GSK-3 inhibition, the method comprising adding a compound of formula (I) to said biological assay and determining the activity of said GSK-3,

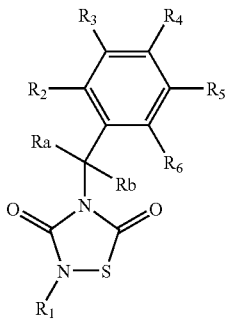

formula I or a pharmaceutically acceptable salt or prodrug thereof;

wherein:

R₁ is a group selected from the group consisting of:

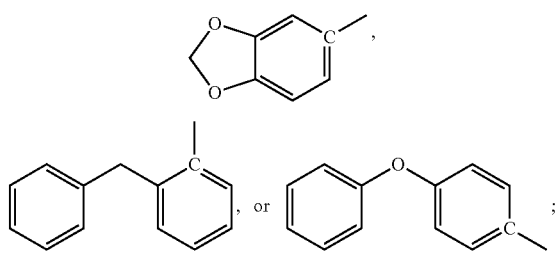

R_a, R_b, R₂, R₃, R₄, R₅, and R₆ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR₇, —C(O)OR₇, —C(O)NR₇R₈, —C=NR₇, —CN, —OR₇, —OC(O)R₇, —S(O)_t—R₇, —NR₇R₈, —NR₇C(O)R₈, —N₂, —N=CR₇R₈ or halogen;

t is 0, 1, 2 or 3; and

R₇ and R₈ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

24. A method of treating a GSK-3 mediated disease or condition selected from the group consisting of amyotrophic lateral sclerosis, multiple sclerosis, Parkinson's disease, progressive supranuclear palsy, subacute sclerosing panencephalitic parkinsonism, postencephalitic parkinsonism, pugilistic encephalitis, corticobasal degeneration, Huntington's disease, frontotemporal dementia, guam parkinsonism-dementia complex, Pick's disease, or AIDS associated dementia, in a patient in need thereof comprising administering to said patient a compound according to formula (I) or a pharmaceutical composition, the method comprising a pharmaceutically acceptable carrier, adjuvant, or vehicle, and a compound according to formula (I)

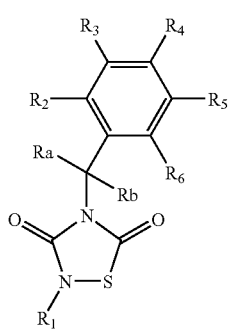

formula I or a pharmaceutically acceptable salt or prodrug thereof;

wherein:

R₁ is a group selected from the group consisting of:

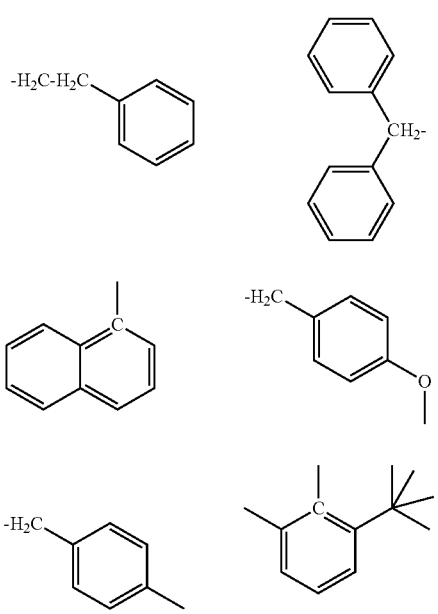

R_a, R_b, R₂, R₃, R₄, R₅, and R₆ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR₇, —C(O)OR₇, —C(O)NR₇R₈, —C=NR₇, —CN, —OR₇, —OC(O)R₇, —S(O)_t—R₇, —NR₇R₈, —NR₇C(O)R₈, —NO₂, —N=CR₇R₈ or halogen;

t is 0, 1, 2 or 3; and

R₇ and R₈ are each independently selected from hydrogen, substituted or unsubstituted substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

25. The method according to claim 24, wherein both R_a and R_b are H.

26. The method according to claim 24, wherein R₂, R₃, R₄, R₅, and R₆ are independently selected from hydrogen, substituted or unsubstituted alkyl, —COR₇, —C(O)OR₇, —OR₇, —NR₇R₈, or halogen, and wherein R₇ and R₈ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

27. The method according to claim 24, wherein R₂, R₃, R₄, R₅, and R₆ are H.

28. The method according to claim 24, wherein the compound of formula (I) is selected from the group consisting of

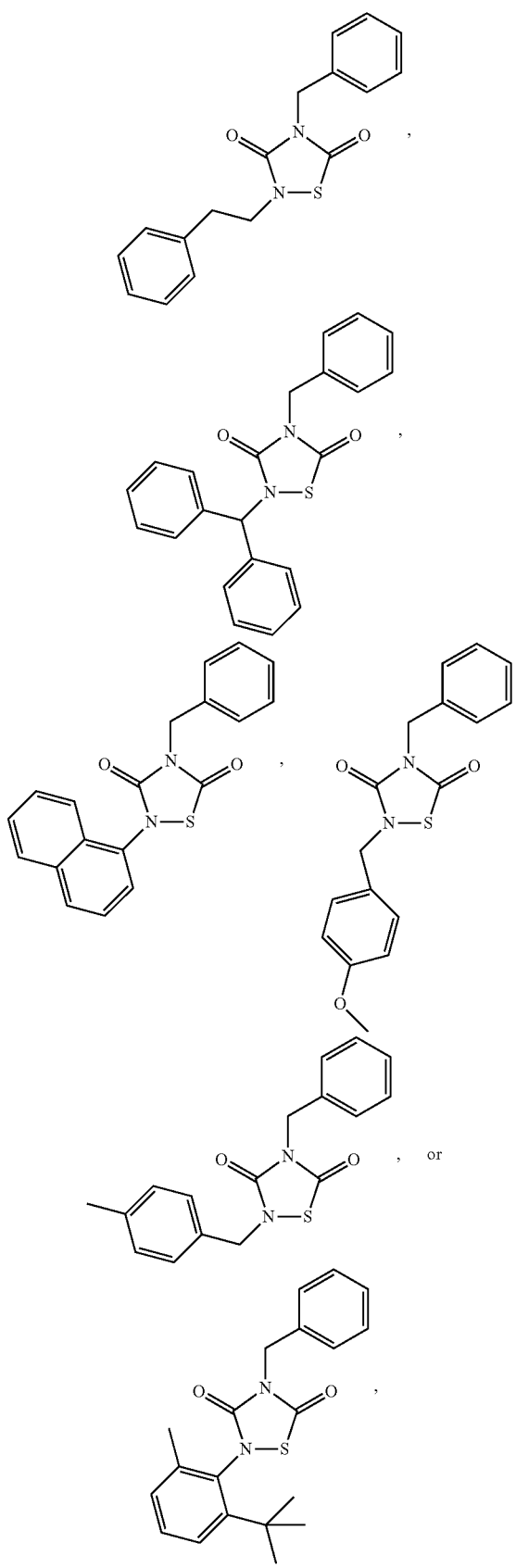

or a pharmaceutically acceptable salt or prodrug thereof.

29. The method according to any one of claims 24 to 28, wherein the disease or condition is selected from the group consisting of amyotrophic lateral sclerosis, or multiple sclerosis.

30. The method according to any one of claims 24 to 28, wherein the disease or condition is selected from the group consisting of Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, or AIDS associated dementia.

31. The method according to claim 30, wherein the disease or condition is progressive supranuclear palsy.

32. A method of treating a GSK-3 mediated disease or condition, selected from neurotraumatic diseases, epilepsy and mood disorders, in a patient in need thereof comprising administering to said patient a compound according to formula (I) or a pharmaceutical composition, the method comprising a pharmaceutically acceptable carrier, adjuvant, or vehicle, and a compound according to formula (I)

formula I

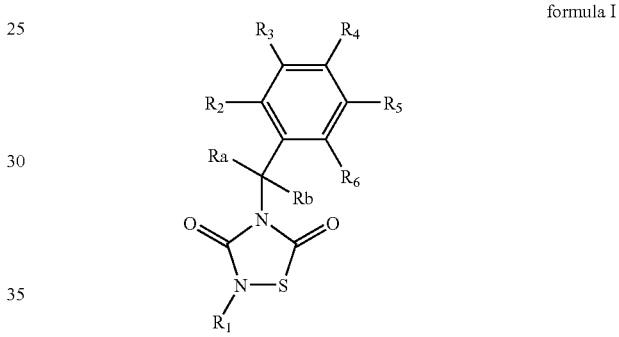

or a pharmaceutically acceptable salt or prodrug thereof; wherein:

$R_1$ is a group selected from the group consisting of:

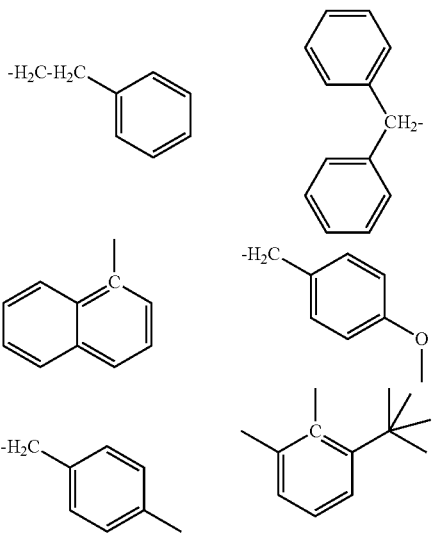

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR$_7$, —C(O)OR$_7$, —C(O)NR$_7$R$_8$, —C=NR$_7$, —CN, —OR$_7$, —OC(O)R$_7$, —S(O)$_t$—R$_7$, —NR$_7$R$_8$, —NR$_7$C(O)R$_8$, —NO$_2$, —N=CR$_7$R$_8$ or halogen;

t is 0, 1, 2 or 3; and

R$_7$ and R$_8$ are each independently selected from hydrogen, substituted or unsubstituted substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

33. The method according to claim 32, wherein both R$_a$ and R$_b$ are H.

34. The method according to claim 32, wherein R$_2$, R$_3$, R$_4$, R$_5$, and R$_6$ are independently selected from hydrogen, substituted or unsubstituted alkyl, —COR$_7$, —C(O)OR$_7$, —OR$_7$, —NR$_7$R$_8$, or halogen, and wherein R$_7$ and R$_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

35. The method according to claim 32, wherein R$_2$, R$_3$, R$_4$, R$_5$, and R$_6$ are H.

36. The method according to claim 32, wherein the compound of formula (I) is selected from the group consisting of

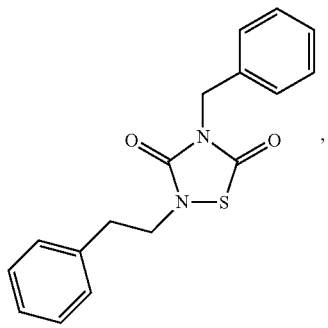

,

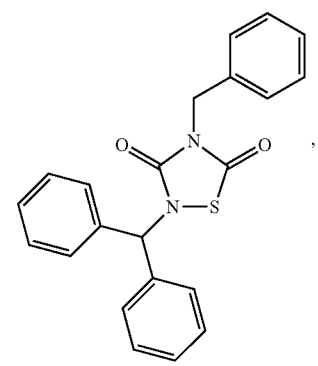

,

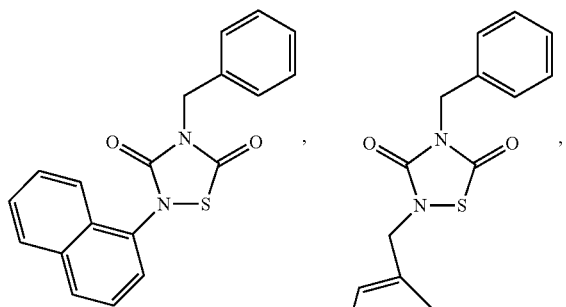

,

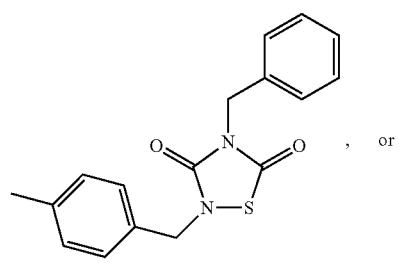

, or

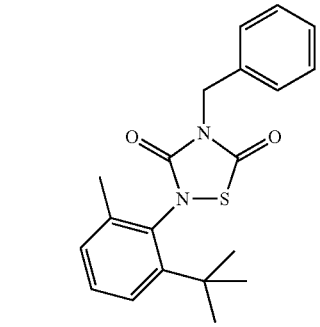

or a pharmaceutically acceptable salt or prodrug thereof.

37. The method according to claim 32, wherein the neurotraumatic disease is acute stroke.

38. The method according to claim 32, wherein the mood disorder is selected from depression, schizophrenia and bipolar disorders.

39. A method of treating a GSK-3 mediated disease or condition which is selected from promotion of functional recovery post stroke, cerebral bleeding, hair loss, obesity, polycystic ovary syndrome, syndrome X, ischaemia, brain injury, leukopenia, Down's syndrome, Lewy body disease, inflammation, and immunodeficiency, in a patient in need thereof, the method comprising administering to said patient a compound according to formula (I) or a pharmaceutical composition comprising a pharmaceutically acceptable carrier, adjuvant, or vehicle, and a compound according to formula (I)

formula I

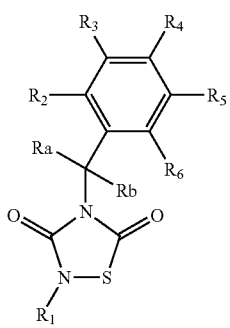

or a pharmaceutically acceptable salt or prodrug thereof; wherein:

$R_1$ is a group selected from the group consisting of:

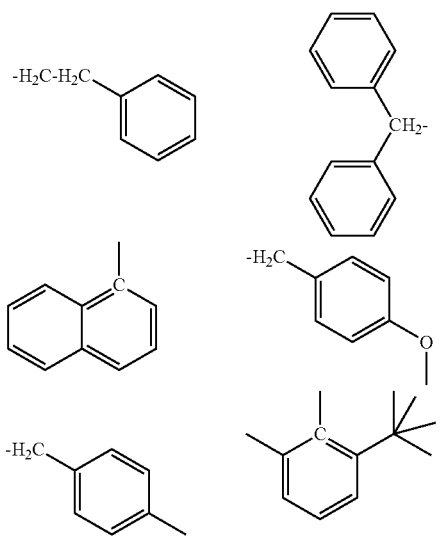

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_7$, —$C(O)OR_7$, —$C(O)NR_7R_8$, —$C\!=\!NR_7$, —CN, —$OR_7$, —$OC(O)R_7$, —$S(O)_t$, —$NR_7R_8$, —$NR_7C(O)R_8$, —$NO_2$, —$N\!=\!CR_7R_8$ or halogen;

t is 0, 1, 2 or 3; and $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

40. The method according to claim 39, wherein both $R_a$ and $R_b$ are H.

41. The method according to claim 39, wherein $R_2$, $R_3$, $R_4$, $R_5$, and $R_6$ are independently selected from hydrogen, substituted or unsubstituted alkyl, —$COR_7$, —$C(O)OR_7$, —$OR_7$, —$NR_7R_8$, or halogen, and wherein $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

42. The method according to claim 39, wherein $R_2$, $R_3$, $R_4$, $R_5$, and $R_6$ are H.

43. The method according to claim 39, wherein the compound of formula (I) is selected from the group consisting of -continued

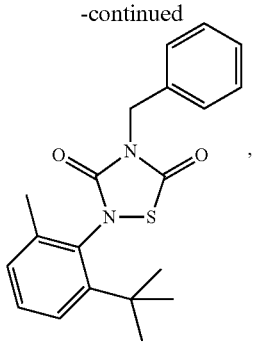

or a pharmaceutically acceptable salt or prodrug thereof.

44. The method according to claim 39, wherein inflammation is a chronic inflammatory disease.

45. The method according to claim 39, wherein brain injury is traumatic brain injury.

46. A method of performing a biological assay for GSK-3 inhibition the method comprising adding a compound of formula (I) to said biological assay and determining the activity of said GSK-3, formula I

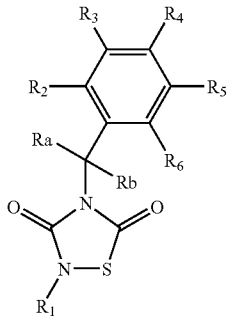

or a pharmaceutically acceptable salt or prodrug thereof; wherein:

$R_1$ is a group selected from the group consisting of:

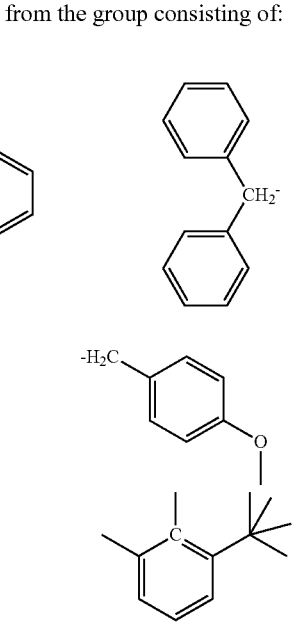

$R_a$, $R_b$, $R_2$, $R_3$, $R_4$, $R_5$, and $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_7$, —$C(O)OR_7$, —$C(O)NR_7R_8$, —$C$=$NR_7$, —CN, —$OR_7$, —$OC(O)R_7$, —$S(O)_t$—$R_7$, —$NR_7R_8$, —$NR_7C(O)R_8$, —$NO_2$, —N=$CR_7R_8$ or halogen;

t is 0, 1, 2 or 3; and $R_7$ and $R_8$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, or halogen.

47. A method of treating a GSK-3 mediated disease or condition, selected from Alzheimer's disease, diabetes or conditions associated with diabetes, cancer, hyperproliferative diseases, hyperplasias, atherosclerotic cardiovascular disease and hypertension, in a patient in need thereof, the method comprising administering to said patient a compound or a pharmaceutical composition comprising a pharmaceutically acceptable carrier, adjuvant, or vehicle, and a compound selected from the group consisting of

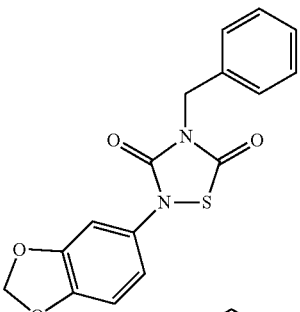

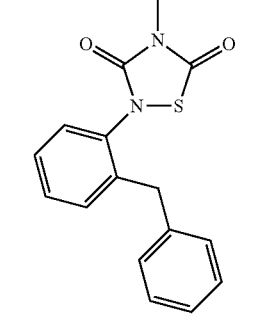

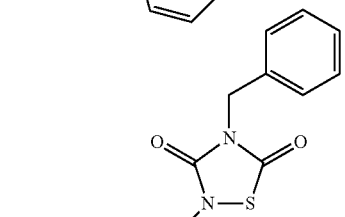

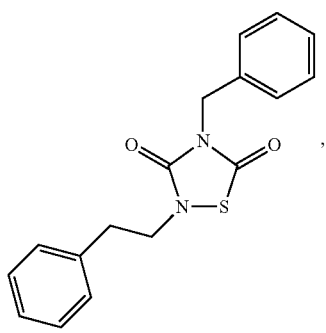

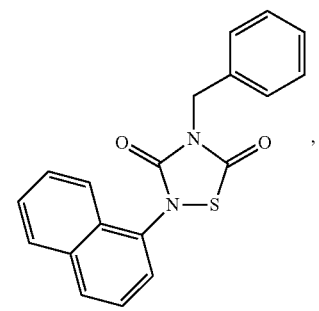

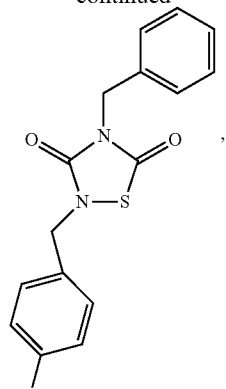

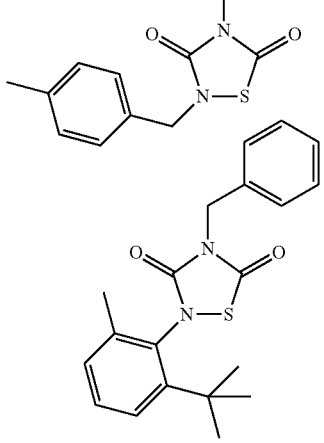

or a pharmaceutically acceptable salt or prodrug thereof.

48. The method according to claim 47, wherein the GSK-3 mediated disease is Alzheimer's disease.

49. The method according to claim 47, wherein the GSK-3 mediated disease is selected from diabetes or conditions associated with diabetes.

50. The method according to claim 49, wherein diabetes is type II diabetes.

51. The method according to claim 47, wherein the GSK-3 mediated disease is selected from cancer, hyperproliferative diseases and hyperplasias.

52. The method according to claim 47, wherein the GSK-3 mediated disease is selected from atherosclerotic cardiovascular disease and hypertension.

* * * * *

UNITED STATES PATENT AND TRADEMARK OFFICE
CERTIFICATE OF CORRECTION

| | |
|---|---|
| PATENT NO. | : 8,158,661 B2 |
| APPLICATION NO. | : 12/428442 |
| DATED | : April 17, 2012 |
| INVENTOR(S) | : Miguel Medina Padilla et al. |

It is certified that error appears in the above-identified patent and that said Letters Patent is hereby corrected as shown below:

Column 7, lines 10-15, the formula on the left reading:

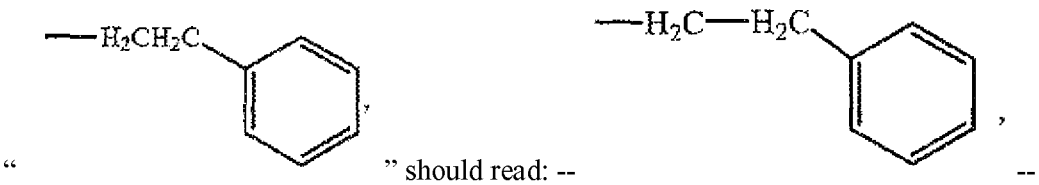

Column 7, lines 26-31, the formula on the right reading:

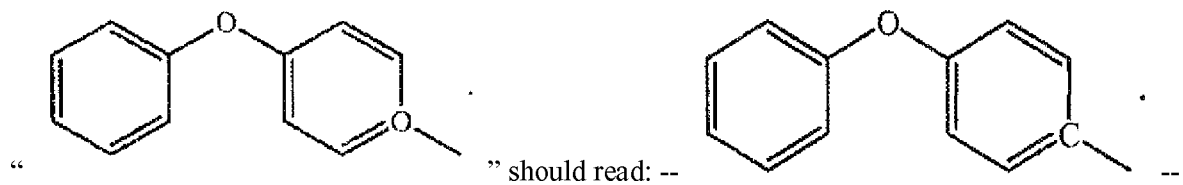

Column 17, lines 16-25, the formula reading:

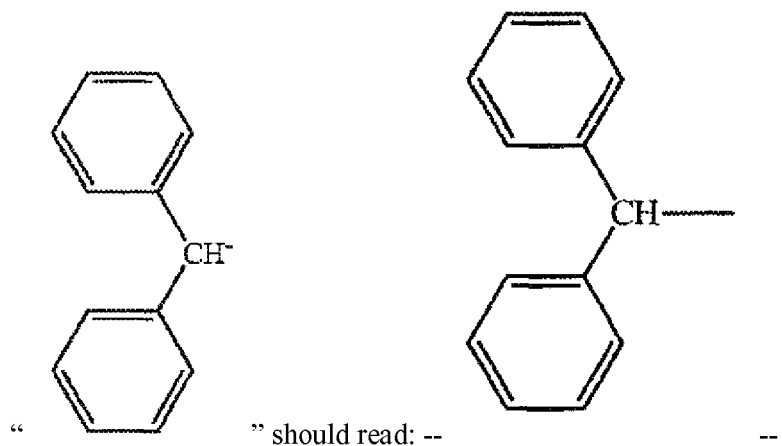

Signed and Sealed this
Fifth Day of June, 2012

David J. Kappos
*Director of the United States Patent and Trademark Office*

Claim 5, column 21, lines 29-58, please delete the two formulas reading:
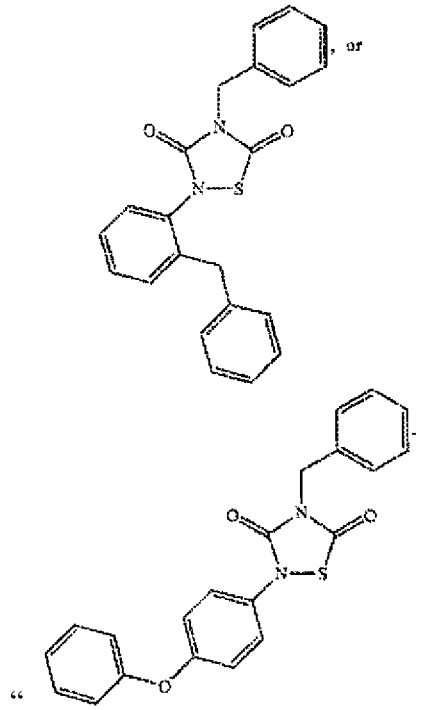
Claim 13, column 23, lines 50-65, and column 24, lines 1-15, please delete the two formulas reading:
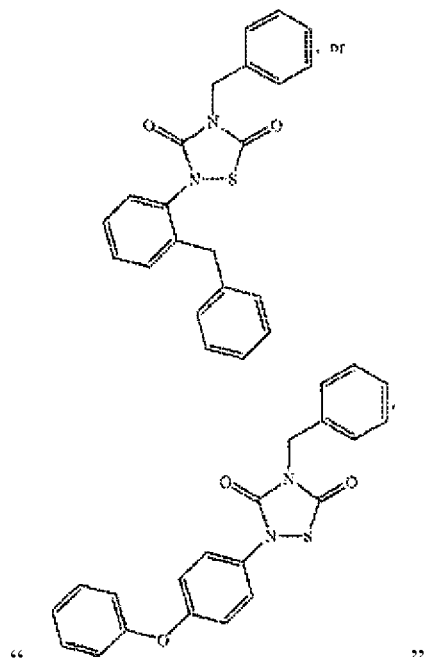

Claim 20, column 26, lines 14-40, please delete the two formulas reading:
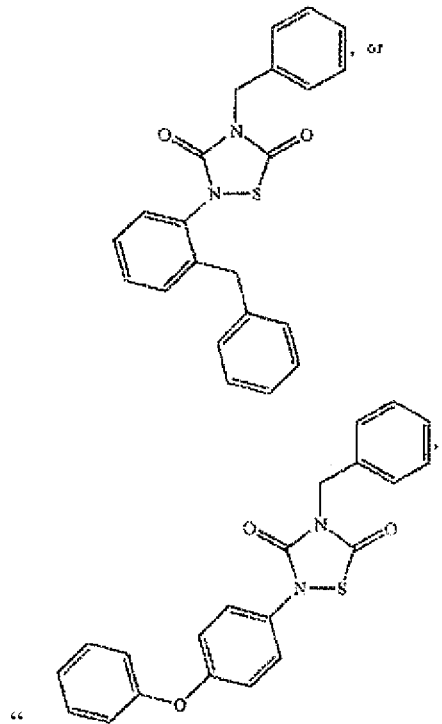
" "
Claim 24, column 28, lines 8-12, the formula on the right reading:
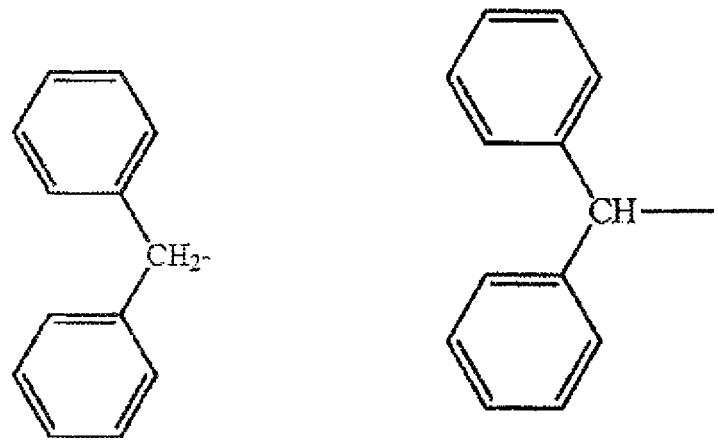
" " should read: -- --
Claim 24, column 28, lines 23-28, the formula on the right reading:
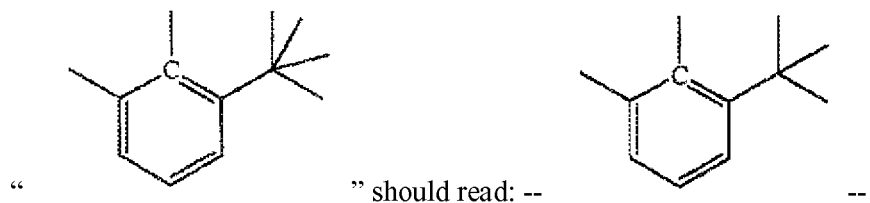
" " should read: -- --

CERTIFICATE OF CORRECTION (continued)
U.S. Pat. No. 8,158,661 B2

Claim 32, column 30, lines 45-51, the formula on the right reading:

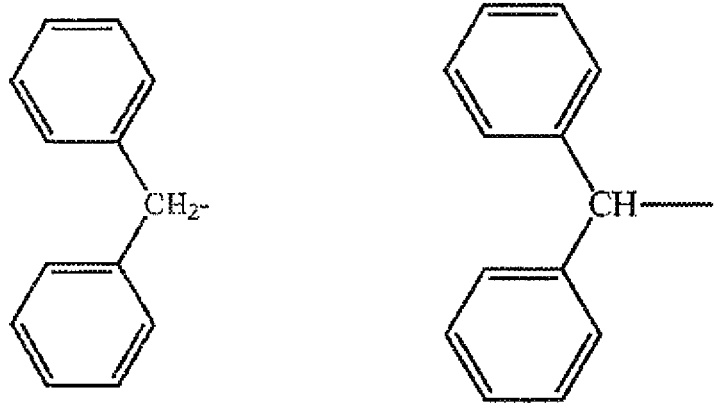

" should read: --                    --

Claim 32, column 30, lines 57-63, the formula on the right reading:

" should read: --                    --

Claim 39, column 33, lines 22-30, the formula on the right reading:

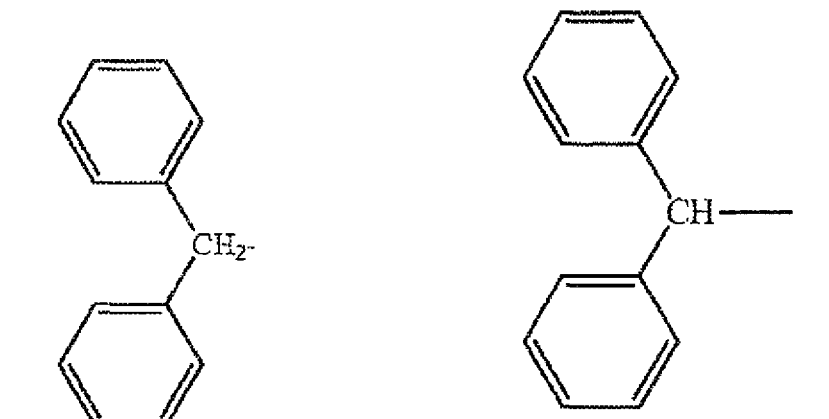

" should read: --                    --

Claim 39, column 33, lines 36-41, the formula on the right reading:

" should read: --                    --

CERTIFICATE OF CORRECTION (continued)
U.S. Pat. No. 8,158,661 B2

Claim 46, column 35, lines 45-54, the formula on the right reading:

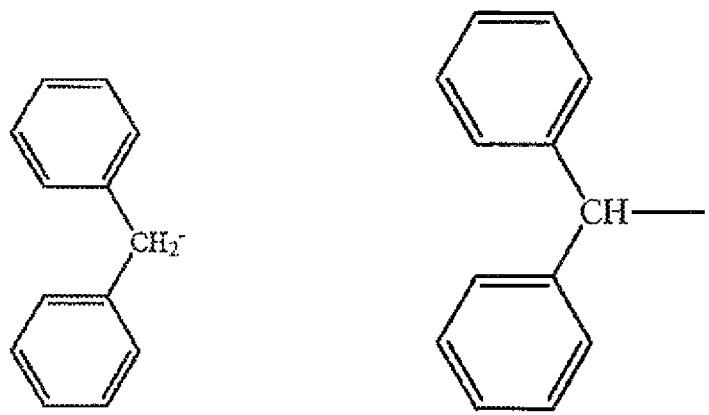

" should read: --                    --

Claim 46, column 35, lines 61-65, the formula on the right reading:

" should read: --                    --